(12) United States Patent
Dave et al.

(10) Patent No.: US 11,096,576 B2
(45) Date of Patent: Aug. 24, 2021

(54) TUNABLE-LENS-BASED REFRACTIVE EXAMINATION

(71) Applicant: PlenOptika, Inc., Cambridge, MA (US)

(72) Inventors: Shivang R. Dave, Boston, MA (US); Daryl Lim, Singapore (SG); Nicholas James Durr, Baltimore, MD (US)

(73) Assignee: PlenOptika, Inc., Cambridge, MA (US)

( * ) Notice: Subject to any disclaimer, the term of this patent is extended or adjusted under 35 U.S.C. 154(b) by 0 days.

(21) Appl. No.: 16/309,169

(22) PCT Filed: Jun. 13, 2017

(86) PCT No.: PCT/US2017/037257
§ 371 (c)(1),
(2) Date: Dec. 12, 2018

(87) PCT Pub. No.: WO2017/218539
PCT Pub. Date: Dec. 21, 2017

(65) Prior Publication Data
US 2019/0313904 A1   Oct. 17, 2019
US 2020/0046222 A2   Feb. 13, 2020

Related U.S. Application Data

(60) Provisional application No. 62/350,018, filed on Jun. 14, 2016.

(51) Int. Cl.
*A61B 3/18* (2006.01)
*A61B 3/00* (2006.01)
(Continued)

(52) U.S. Cl.
CPC ............... *A61B 3/18* (2013.01); *A61B 3/005* (2013.01); *A61B 3/0008* (2013.01);
(Continued)

(58) Field of Classification Search
CPC ......... A61B 3/09; A61B 3/103; A61B 3/1208; A61B 3/0008; A61B 3/0033; A61B 3/005;
(Continued)

(56) References Cited

U.S. PATENT DOCUMENTS 4,943,162 A   7/1990   Sims
5,420,651 A   5/1995   Kamppeter
(Continued)

FOREIGN PATENT DOCUMENTS

CN   105578947 A   5/2016
EP     3387985 A1  10/2018
(Continued)

OTHER PUBLICATIONS

Notification of Transmittal of the International Search Report and the Written Opinion of the International Searching Authority for International Application No. PCT/US2017/037257, titled "Tunable-Lens-Based Refractive Examination," dated Nov. 29, 2017.
(Continued)

*Primary Examiner* — Jordan M Schwartz
(74) *Attorney, Agent, or Firm* — Hamilton, Brook, Smith & Reynolds, P.C.

(57) ABSTRACT

An apparatus, and corresponding method, for determining a refractive property of an eye includes a housing with a port configured to receive an eye and also light from the eye. A tunable lens can be mounted to the housing to apply a variable focal power to the light from the eye and to pass the light along an optical path toward a wavefront sensor within the housing. The wavefront sensor can receive the light via the optical path and measure a wavefront thereof. A determination module can be configured to determine a property of the eye based on the wavefront. Embodiments can be handheld, portable, and open view, while providing objec-
(Continued)

tive wavefront aberrometry, subjective phoroptry, and accommodation and presbyoptic evaluation, as well as lensometry functions.

27 Claims, 20 Drawing Sheets

(51) Int. Cl.
| | |
|---|---|
| *A61B 3/09* | (2006.01) |
| *A61B 3/103* | (2006.01) |
| *A61B 3/12* | (2006.01) |
| *A61B 3/028* | (2006.01) |

(52) U.S. Cl.
CPC ............ *A61B 3/0033* (2013.01); *A61B 3/028* (2013.01); *A61B 3/0285* (2013.01); *A61B 3/09* (2013.01); *A61B 3/103* (2013.01); *A61B 3/1208* (2013.01)

(58) Field of Classification Search
CPC ....... A61B 3/0075; A61B 3/0091; A61B 3/02; A61B 3/028; A61B 3/0285; A61B 3/032; A61B 3/18
See application file for complete search history.

(56) References Cited

U.S. PATENT DOCUMENTS

| | | | |
|---|---|---|---|
| 5,684,561 A | 11/1997 | Yancey | |
| 6,517,203 B1 | 2/2003 | Blum et al. | |
| 6,688,745 B2 | 2/2004 | Ross et al. | |
| 6,709,108 B2 | 3/2004 | Levine et al. | |
| 6,986,579 B2 | 1/2006 | Blum et al. | |
| 6,988,801 B2 | 1/2006 | Yoon | |
| 7,357,509 B2 | 4/2008 | Williams et al. | |
| 7,993,399 B2 | 8/2011 | Peyman | |
| 8,409,278 B2 | 4/2013 | Peyman et al. | |
| 9,427,156 B1 | 8/2016 | Steven et al. | |
| 9,462,939 B2 | 10/2016 | Abitbol et al. | |
| 9,681,800 B2 | 6/2017 | Schwiegerling et al. | |
| 9,895,058 B2 | 2/2018 | Baker et al. | |
| 9,980,638 B2 | 5/2018 | Keita et al. | |
| 2003/0071969 A1 | 4/2003 | Levine et al. | |
| 2003/0100703 A1 | 6/2003 | Cox et al. | |
| 2004/0100617 A1 | 5/2004 | Abitbol | |
| 2006/0203196 A1* | 9/2006 | Van Heugten | A61B 3/103 351/221 |
| 2008/0284979 A1 | 11/2008 | Yee et al. | |
| 2009/0002632 A1 | 1/2009 | Vogelsang et al. | |
| 2012/0038883 A1 | 2/2012 | Peyman et al. | |
| 2012/0287398 A1 | 11/2012 | Baker et al. | |
| 2013/0135581 A1 | 5/2013 | Lai | |
| 2013/0182224 A1 | 7/2013 | Schwiegerling et al. | |
| 2015/0042957 A1* | 2/2015 | Abitbol | A61B 3/0285 351/235 |
| 2016/0310000 A1* | 10/2016 | Meneghini | A61B 3/0075 |
| 2017/0172406 A1* | 6/2017 | Pamplona | A61B 3/0025 |
| 2018/0078131 A1 | 3/2018 | Durr et al. | |
| 2018/0263488 A1* | 9/2018 | Pamplona | A61B 3/0008 |

FOREIGN PATENT DOCUMENTS

| | | |
|---|---|---|
| JP | 2005-506866 A | 3/2005 |
| JP | 2009-093201 A | 4/2009 |
| WO | 2004049927 A1 | 6/2004 |
| WO | 2005037090 A1 | 4/2005 |
| WO | 2006092802 A2 | 9/2006 |
| WO | 2014169148 A1 | 10/2014 |
| WO | 2015003062 A1 | 1/2015 |
| WO | 2015003086 A1 | 1/2015 |
| WO | 2017218539 A1 | 12/2017 |

OTHER PUBLICATIONS

Notification Concerning Transmittal of International Preliminary Report on Patentability and the Written Opinion of the International Searching Authority for International Application No. PCT/US2017/037257, titled "Tunable-Lens-Based Refractive Examination," dated Dec. 18, 2018.
Adaptica, VisionFit, retrieved online on Apr. 21, 2017 at http://www.adaptica.com/products/visionfit/, 15 pages.
Cervino, et al., "Wavefront Analyzers Induce Instrument Myopia," Journal of Refractive Surgery, Oct. 2006, vol. 22, Issue 8: 795-803.
Marks, et al., "Adjustable adaptive compact fluidic phoropter with no mechanical translation of lenses," Optics Letters, vol. 35, No. 5, Mar. 1, 2010.
Newman, J., "Here's how the consumer Oculus Rift got so much lighter and comfier," retrieve online on Jun. 5, 2017 at https://www.pcworld.com/article/3050432/heres-how-the-consumer-oculus-rift-got-so-much-lighter-and-comfier.html, Mar. 31, 2016.
Bozic, James, "Measuring the Accomodative Convergence to Accomodation (AC/A) Ration with the Grand Seiko WR-5100K," American Academy of Optometry, Retrieved from Internet at: https://www,aaopt.org/detail/knowledge-base-article/measuring-accomm . . . (2001), Retrieved from Internet on: Jul. 2, 2021, 3 pages.
Cheng, et al., "Predicting subjective judgement of best focus with objective image quality metrics," *Journal of Vision, 4*: 310-321 (2004).
Davies, "Cliniical Evaluation of the Shin-Nippon NVision-K 5001/Grand Seiko WR-5100K Autorefractor," Retrieved from the Internet at: https://journals.lww.com/optvissci/Abstract/2003/04000/Clinical_Evalus . . . (Apr. 2003), Retrieved from the Internet Internet on: Jul. 2, 2021, 4 pages.
Durr, et al., "Design and Clinical Evaluation of a Handheld Wavefront Autorefractor," Optonetry and Vision Science, 92(12): 8 pages (2015).

\* cited by examiner

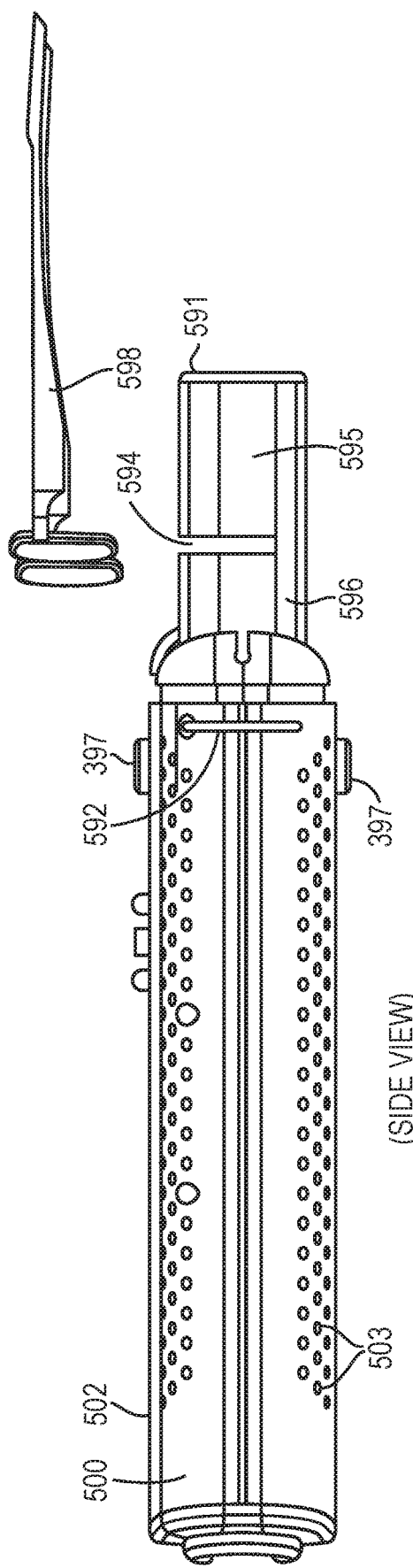
FIG. 5B (SIDE VIEW)
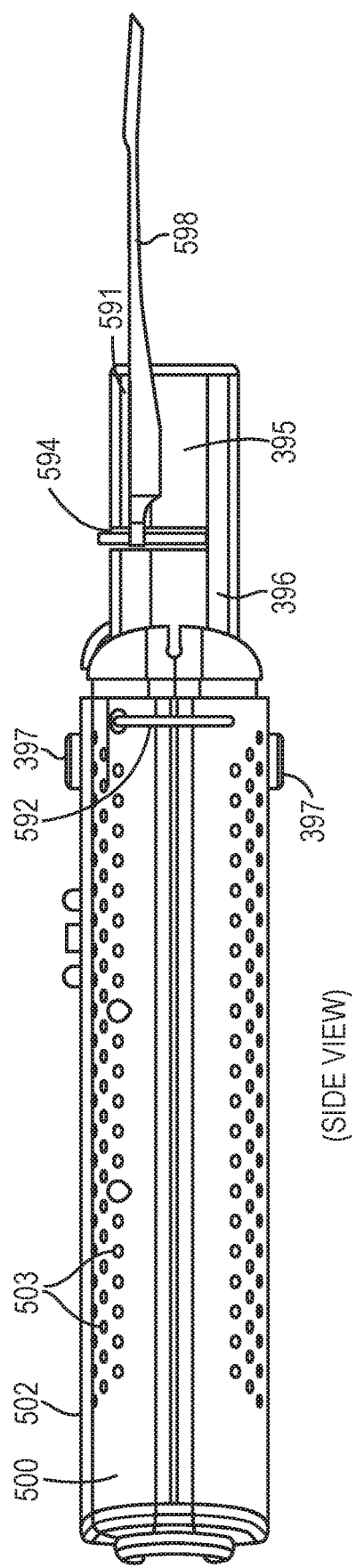
FIG. 5C (SIDE VIEW)

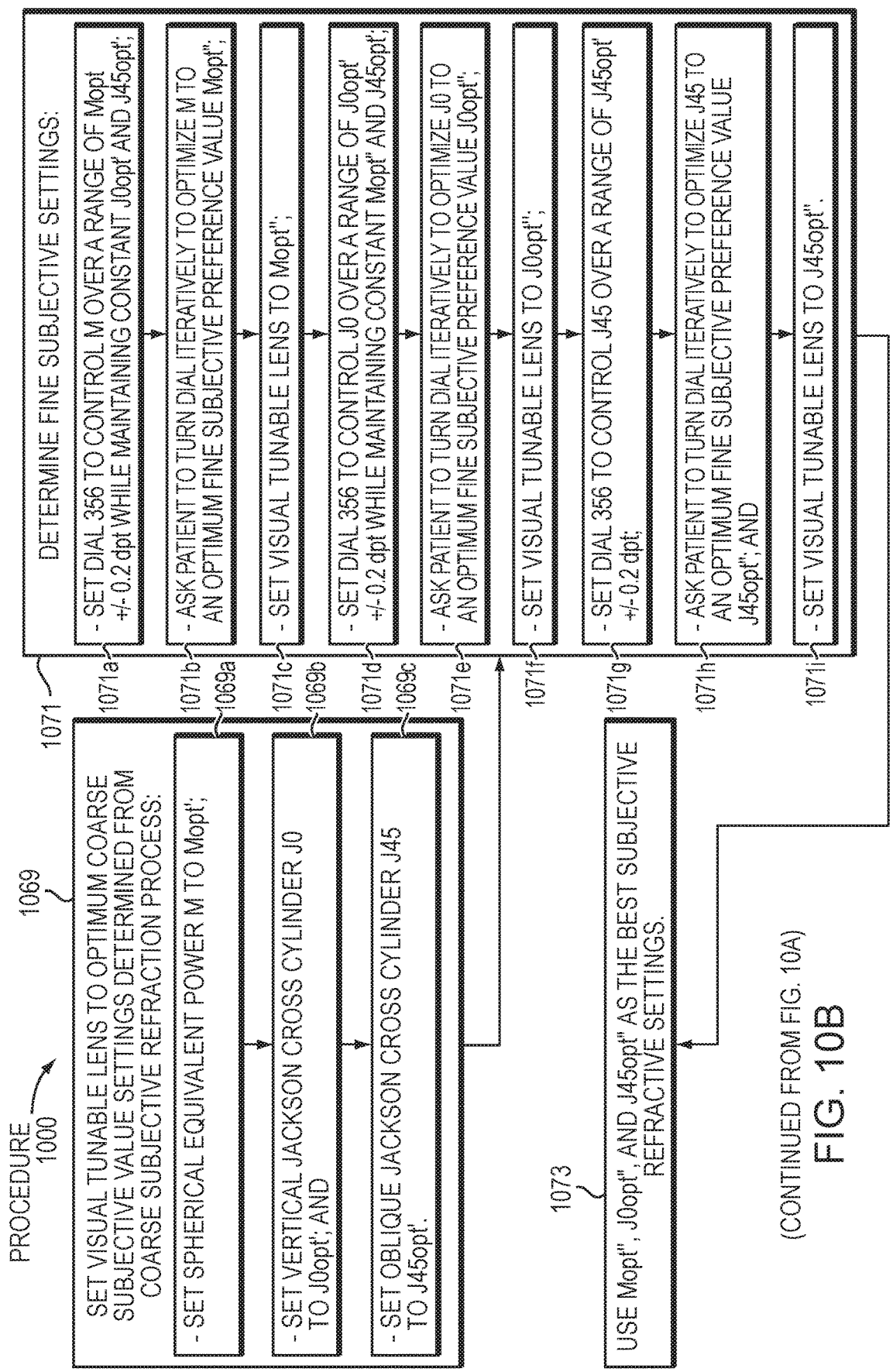
FIG. 10B
(CONTINUED FROM FIG. 10A)

TUNABLE-LENS-BASED REFRACTIVE EXAMINATION

RELATED APPLICATIONS

This application is the U.S. National Stage of International Application No. PCT/US2017/037257, filed Jun. 13, 2017, which designates the U.S., published in English, and claims the benefit of U.S. Provisional Application No. 62/350,018, filed on Jun. 14, 2016. The entire teachings of the above Applications are incorporated herein by reference.

GOVERNMENT SUPPORT

This invention was made with government support under SBIR 1R43EY025452-01A1 and SBIR 2R44EY025452-02A1 from the National Eye Institute of the National Institutes of Health. The government has certain rights in the invention.

BACKGROUND

Optometrists or ophthalmologists performing eye examinations in a clinic typically use a phoropter (or equivalently, a trial lens set) to determine which of many fixed lens settings produces the best eyesight, subjectively, for a given patient. However, this is a lengthy process due to the iterative nature of the subjective refraction. To speed up the process, objective measurements using a separate instrument are often used to reduce the number of iterations needed for subjective refraction with the phoropter. The relatively quick objective measurement of the refractive status of the eye serves as a good starting point for subjective refraction. Autorefractors are a common tool to perform such objective measurements of the eye. Wavefront aberrometers are a type of autorefractor which have been used in clinics to make objective determinations of eye aberrations. However, because wavefront aberrometers are typically more complex and expensive than other types of autorefractors, they have not typically been used for providing an initial starting for subjective refraction. Besides typical aberrations used for prescribing eyeglasses (defocus and astigmatism), wavefront aberrometry can also determine aberrations of higher order than phoroptry.

More recently, portable devices for performing wavefront aberrometry have been developed. These devices have the potential advantage of making refractive eye care more available and affordable, particularly in locations with few eye care providers.

SUMMARY

Existing portable wavefront aberrometers have several disadvantages. First, they do not allow a patient to view through the device so that the patient's eyes can automatically tend toward a relaxed, unaccommodated state. To counter this, cycloplegic drops can be used to disable accommodation. However, this treatment includes side effects and requires waiting time between treatment and aberrometry measurements. Another approach to relaxing accommodation is to "fog" the eye. However, this approach also has limitations and is not effective for all eye patients.

Furthermore, existing portable wavefront aberrometers (i) do not provide phoroptry measurements, which take into account a patient's subjective preference, which is typically slightly different from the correction indicated by purely objective measurements, or (ii) are not open view, allowing a patient to see through the device to a target external and spaced away from the device. Phoropters are typically large, bulky, heavy, and involve motion and vibration when lenses are switched, and all of these characteristics are undesirable in environments where handheld devices are used. While subjective refraction is considered the "gold" standard in evaluating patients for refractive correction, the phoropter is usually not used in environments where handheld portable wavefront aberrometers are employed. Instead, trial frames and lenses are used, which can be slower and more cumbersome to use.

While tunable lenses have been proposed for use with certain worn or portable devices, it is known that tunable lenses in many instances lack the precision of fixed lenses. Yet even with a multiple-fixed-lens phoropter-type system, wavefront aberrometry is still highly desirable for determining both lower- and higher-order corrections objectively, and the phoroptry and wavefront aberrometry functions have conventionally been performed using separate devices.

Embodiments described herein can overcome the limitations of existing, separate phoroptry and wavefront aberrometry systems by performing the same functions in the same unit. Furthermore, in many respects, better eye analysis and examination is possible using embodiment apparatuses and methods than is possible with two separate instruments for phoroptry and wavefront aberrometry, whether in a clinical setting or a field-use setting. Example advantages of embodiments include increased examination speed, more accurate refractive results, increased flexibility in patient and clinician use, and the ability to obtain wavefront aberrometry measurements at arbitrary times during phoroptry and accommodation measurements. Moreover, embodiments including portable apparatuses can even be configured to perform lensometry measurements. Embodiment apparatuses and methods can also provide patients with an indication of how their vision will improve with lenses having refractive corrections that are determined by the same system based on objective wavefront aberrometry, subjective phoroptry measurements, or both.

Furthermore, embodiments described herein can overcome the limitations of existing portable wavefront aberrometers by providing open-view, binocular configurations that do not necessarily require the use of cycloplegic drops or fogging. Embodiment devices and methods can include using one or more tunable lenses incorporated into a device to improve the accuracy of wavefront aberrometry measurements, perform subjective phoroptic measurements, simulate final refractive correction for the patient, and perform lensometry measurements. Thus, by combining a wavefront sensor and a tunable lens, embodiments described herein can achieve many advantages that have not been achievable with existing devices that seek to use either one or the other, and these advantages will become more apparent throughout the description hereinafter.

In one embodiment, an apparatus for determining a property of an eye, and corresponding method, includes a housing having a port configured to receive an eye (i.e., to serve as a viewing port through which an eye being assessed can view) and to receive light from the eye. Light can be received from the eye by directing a source of eye illumination light from the apparatus into the eye and then collecting light that is thereby reflected or backscattered from the eye, for example. The property of the eye can be a refractive property such as a lower- or higher-order refractive aberration, a refractive prescription, an accommodation range, or another refractive property related to eyesight.

The apparatus further includes a visual tunable lens mounted to, or configured to be mounted to, the housing to apply a variable focal power to the light from the eye and to pass the light along an optical path. The apparatus also includes a wavefront sensor within the housing, the wavefront sensor being configured to receive the light from the eye via the optical path and to measure a wavefront of the light from the eye. The apparatus still further includes a determination module configured to determine a property of the eye based on the wavefront. The property of the eye can be a refractive prescription needed to correct the vision of the eye, a spherical aberration, a cylindrical aberration, an axis for cylindrical aberration, a refractive error of higher order than spherical or cylindrical aberrations (i.e., defocus and astigmatism), a range of accommodation, an objective refractive measurement, a subjective refractive preference of a person having the eye, or other property of the eye.

The housing can be configured to be gripped by at least one hand of the person having the eye (i.e., the person whose eye is to be assessed using the apparatus) to support a full weight of the apparatus during use. The port can be further configured to receive a corrective lens applied to the eye, and the wavefront sensor can be further configured to measure the wavefront of the light from the eye in combination with the corrective lens. The port can be a first port, the eye can be a first eye, and the housing can further include a second port configured to receive a second eye of the same person (whose eye is to be assessed using the apparatus), wherein the housing defines a binocular configuration.

The visual tunable lens can be a first visual tunable lens, and the apparatus can further include a second visual tunable lens configured to be mounted to the housing and to apply a variable focal power to light from the second eye.

The port can be a proximal port, and the housing can further includes a distal port, the proximal and distal ports together forming a visual channel from the proximal port through the distal port, the visual channel providing an open view to enable the eye to see target indicia external to and spaced away from the housing through the visual channel.

The apparatus may also include a target light source mounted to the housing and configured to produce the target indicia external to and spaced away from the housing, the target indicia being viewable by the eye through the visual channel. The target light source can be further configured to produce the target indicia at a distance of effective infinity from the eye.

The apparatus can further include an eye illumination light source in the housing, and the eye illumination light source can be configured to direct light through the proximal port and into the eye to produce the light from the eye via reflection or backscattering from the eye. A light source tunable lens can also be included in the apparatus and can be configured to apply a variable focal power to light from the eye illumination light source. The light source tunable lens can be further configured to randomize a speckle pattern produced by the eye illumination light source at the eye or a speckle pattern produced by the light from the eye at the wavefront sensor. The port may be further configured to receive the light from the eye non-collinearly with respect to the light from the illumination light source directed through the port and into the eye. Light from the eye illumination light source can be restricted by an aperture that can be included in the apparatus, and a diameter of the aperture can be between about 50 µm and about 500 µm.

The visual tunable lens can be configured to randomize a speckle pattern produced by the eye illumination light source at the eye or a speckle pattern produced by the light from the eye at the wavefront sensor. The visual tunable lens can be further configured to be situated at a spectacle plane of the eye with the proximal port having received the eye.

The determination module may be further configured to determine a refractive correction to be applied to the eye, or to determine one or more wavefront errors of higher order than defocus and astigmatism. The determination module can be further configured to determine a lens wavefront error due to the visual tunable lens for calibration, or to determine an accommodation range of the eye as a function of a plurality of wavefront measurements of the light from the eye.

The housing can be configured to receive a lensometer attachment, and the lensometer attachment may be configured to support a corrective lens intended to be worn by a person, or a lens blank intended to be manufactured into a corrective lens. The determination module can be further configured to determine to determine a refractive property of the corrective lens or lens blank based on a lens wavefront of light received through the corrective lens or lens blank.

The apparatus can further include a closed-loop control circuit configured to adjust the variable focal power of the visual tunable lens iteratively in response to successive wavefront measurements to minimize a wavefront error of the light from the eye. The apparatus can further include a control circuit configured to adjust the visual tunable lens in accordance with a subjective refractive preference of a person having the eye. The apparatus can also include a manual control configured to be adjustable by a person having the eye, or someone else helping the person having the eye, to adjust the variable focal power of the visual tunable lens in accordance with a subjective refractive preference of a person having the eye.

The apparatus can include a reporting interface configured to report a prescription for refractive correction of the eye. The apparatus can also include a communication interface configured to query a person having the eye, or receive a response from the person, regarding a subjective, refractive preference. The apparatus can also include a fixed lens configured to be attached to the housing and to apply a fixed focal power to the light from the eye to shift a range of refractive correction measurement of the apparatus, or a fogging lens configured to be attached to the housing and to fog a view of the eye.

The sensor module or determination module can include a cellular phone, or the apparatus can further include a cellular phone configured to be attached to the housing or to display a representation of the wavefront of the light from the eye. The wavefront sensor can include a pixel array of a cellular phone.

The apparatus can also include cross-polarizers disposed within the optical path.

The visual tunable lens can be further configured to apply a variable spherical power, astigmatic power, and axis mutually independently. The visual tunable lens can be further configured to apply a spherical equivalent power, vertical Jackson cross cylinder, and oblique Jackson cross cylinder mutually independently. The visual tunable lens can include at least one of a liquid-filled lens, an electro-wetting lens, an Alvarez lens pair, spatial light modulator, deformable mirror, lens with power that varies spatially, a multi-lens system that changes lens distances to tune optical power, or a tunable Fresnel lens. The visual tunable lens can include a two-element optic configured to apply the variable focal power as a function of lateral or rotational displacement of the two elements with respect to each other.

The property of the eye can be an objective property based on the wavefront, and the determination module can be further configured to predict a subjective refractive preference of a person having the eye based on the objective property. The determination module can be further configured to predict the subjective refractive preference based further on a demographic or physical attribute of a person having the eye. Demographic attributes can include at least one of an age, gender, ethnicity, weight, height, occupation, or another demographic attribute of the person having the eye. Physical attributes can include at least one of a retinal image quality, axial length, iris color, topography, corneal curvature, aberration of higher order than spherical or cylindrical aberration, or another attribute of the eye. The determination module can be further configured to predict the subjective refractive preference using a correlation developed from a database including respective demographic or physical attributes and respective objective eye properties of a plurality of eye patients.

In another embodiment, a method for determining a property of an eye, and corresponding apparatus, includes applying a variable focal power to light received from an eye, via a port of a housing configured to receive the eye, using a visual tunable lens. The method also includes passing the light from the eye along an optical path, as well as measuring a wavefront of the light from the eye, the light received via an optical path from the port. The method further includes determining a property of the eye based on the wavefront of the light from the eye.

BRIEF DESCRIPTION OF THE DRAWINGS

FIGS. 5B-5C are side-view illustrations of the apparatus illustrated in FIG. 5A. FIG. 5B shows eyeglasses outside of the lensometer module, while FIG. 5C shows the eyeglasses inserted into the lensometer attachment.

FIG. 5F is a side-view illustration of the assembly, FIG. 5G is a perspective-view of the assembly, and FIG. 5H is an end-view illustration of the assembly;

FIGS. 5I-5K are various illustrations showing the calibration cradle attached to the apparatus illustrated in FIGS. 5A-5C.

FIGS. 10A-10B are flow diagrams illustrating parts of a single procedure for determining subjective refractive measurements (phoroptry) for refractive eye correction using embodiment devices directly interacting with a patient.

Figure 1:
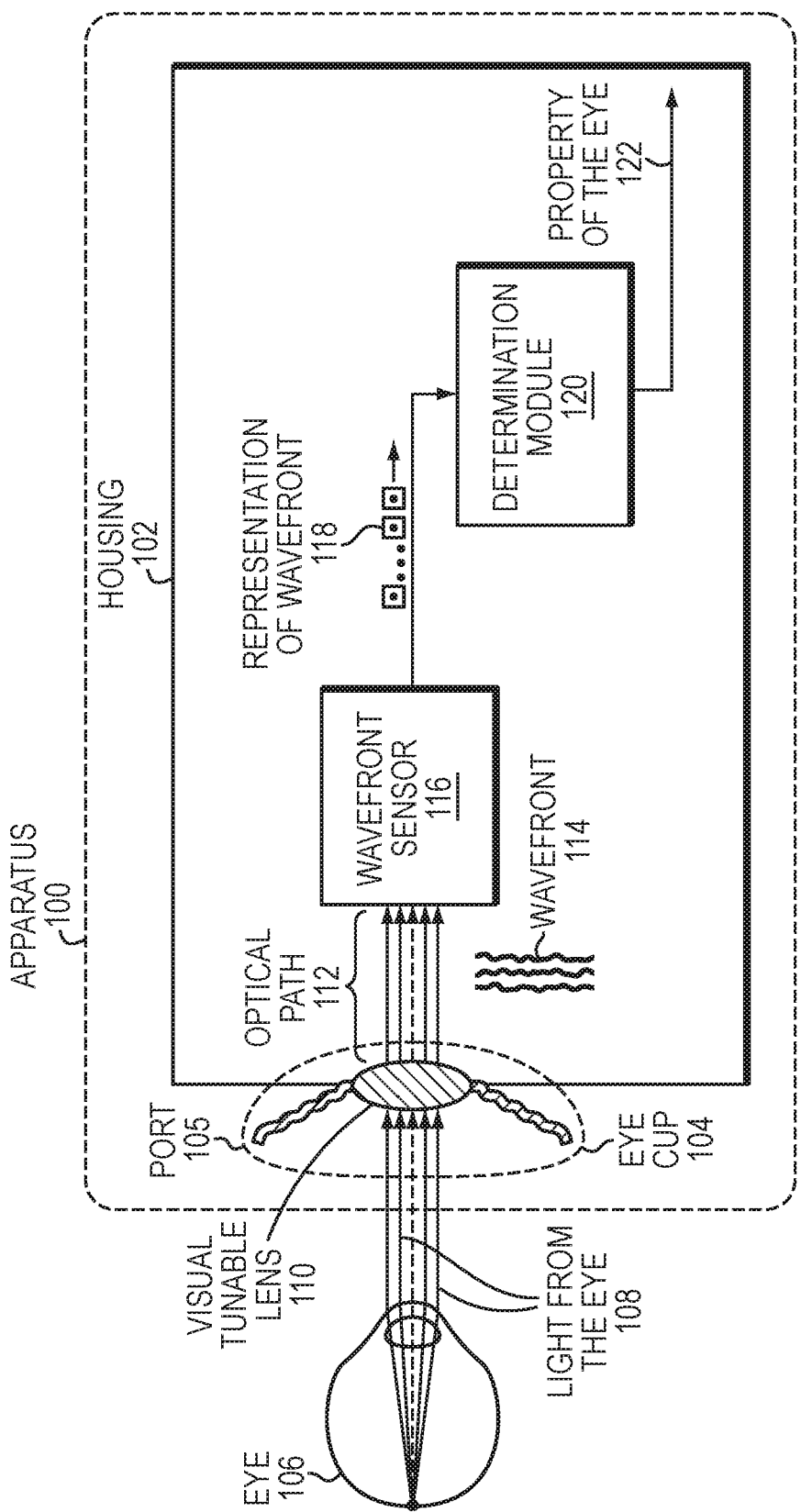
FIG. 1 is a schematic block diagram illustrating an embodiment apparatus for determining a property of an eye.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION

A description of example embodiments of the invention follows.

Refractive eye examinations by an optometrist or ophthalmologist typically involve using a phoropter to determine which of many fixed lens settings produces the best eyesight, subjectively, for a given patient. Clinical phoropters are usually binocular (enabling both of a patient's eyes to view through separate sets of lenses) and open-view (enabling a patient to view, through the phoropter lenses, a distant target pattern). Typically, the patient is asked to focus on a target pattern situated a distance of about 20 feet from the patient's eye. The open-view design also performs the important function of encouraging the patient's eyes to remain unaccommodated (relaxed and as optimized as possible for long-distance viewing) during the measurement. The unaccommodated state is an important clinical prerequisite for accurate measurements for refractive correction of distance vision. Thus, using typical clinical phoropters, a prescription for refractive correction can be obtained that both (i) corrects for important types of optical aberrations of the eyes and (ii) takes into account a patient's subjective feedback about which correction is preferable.

Wavefront aberrometers, in contrast to clinical phoropters, determine a refractive correction for a patient objectively, without input from the patient, based on sensing a wavefront of near infrared (near-IR) directed into the eye and reflected or scattered from the retina of the eye. Wavefront aberrometry in an eye clinic can provide information about aberrations of the eye of higher order than just sphere and cylinder and is considered a valuable tool in determining refractive correction.

Handheld devices have been developed more recently to perform wavefront aberrometry. A goal of these devices is to enable refractive examination of people in remote areas without access to standard clinics or eye care professionals, as well as to decrease cost of examination and limit the number of expensive instruments required, as well as to streamline the refractive examination in high-resource settings. Handheld wavefront aberrometer devices have some limitations, in that they do not take into account subjective feedback from an eye patient. Further, high-quality clinical phoropters may not be available to supplement handheld device measurements, due to the cost, size, weight, and mobility limitations of standard phoropters.

Moreover, an important clinical requisite for an accurate measurement is that the patient's eye should be relaxed while the measurement is made. Since existing handheld devices do not allow a patient to view through them and focus on a distant object to cause eye relaxation, there are a number of other techniques that have been used to induce relaxation using existing non-open view devices. For example, cycloplegic drops can be placed in the eye to paralyze accommodative control. While effective, these drugs may often have side effects that can be undesirable for the patient and can require 15 minutes or more for their effects to occur. Another approach is to place lenses in front of the patient's eyes to simulate myopia (i.e. shortsightedness), referred to as "fogging" the patient, so that the patient's eye(s) are coerced into relaxing their accommodation so as to bring a fixation target into focus. While fogging can be effective for many patients, some others may not respond well to this technique. Furthermore, these techniques, even when effective, still do not produce exactly the same results as actually allowing a patient to view a distant target through an open view lens, as is done with standard clinical phoropters.

Including a set of physical lenses, similar to those of a phoropter, with a handheld device has been attempted. However, this increases cost, weight, and system complexity, and this solution also has feasibility challenges because switching between lenses requires at least some mechanical motion or disturbance of a portable handheld device. Thus, this approach would be less mechanically robust and prone to breaking or mis-alignment. Alternative optical approaches such as adaptive optics (e.g., deformable mirrors, spatial light modulators) are prohibitively expensive for application in low-cost diagnostics.

Embodiment apparatus examples can include one or more tunable lenses integrated into a handheld wavefront aberrometer to act effectively as an on-board phoropter. Wavefront aberrometer measurements can be used as feedback to the tunable lens, in closed-loop fashion, to automatically and quickly adjust a tunable lens through which the patient views to optimize vision objectively. Because the tunable lens can iteratively correct measured wavefront errors until the measured wavefront is nominally parallel, objective wavefront evaluations can be made with greater accuracy.

As will be understood by those familiar with Hartmann-Shack wavefront sensors, for example, when the wavefront is nominally parallel, a spot pattern produced by the sensor has spots nominally uniformly spaced. In this state, uniformity of the spot pattern (and, hence, wavefront errors) can be more exactly evaluated than if the spot pattern is very distorted.

After objective autorefraction, feedback from a patient can be used to further adjust the tunable lens in accordance with subjective patient preference to improve the proposed correction. An apparatus can communicate with a patient through a variety of methods to obtain the subjective feedback, even automatically or semi-automatically. This feedback can be obtained and implemented in embodiment devices with or without the assistance of a technician or other eye professional. Embodiments can be designed to be self-usable by a single user (i.e., eye patient) without assistance from a clinician (e.g., an ophthalmologist, optometrist, clinical assistant, field technician, or any other person working to assist an eye patient to obtain a corrective prescription).

Figure 10A:
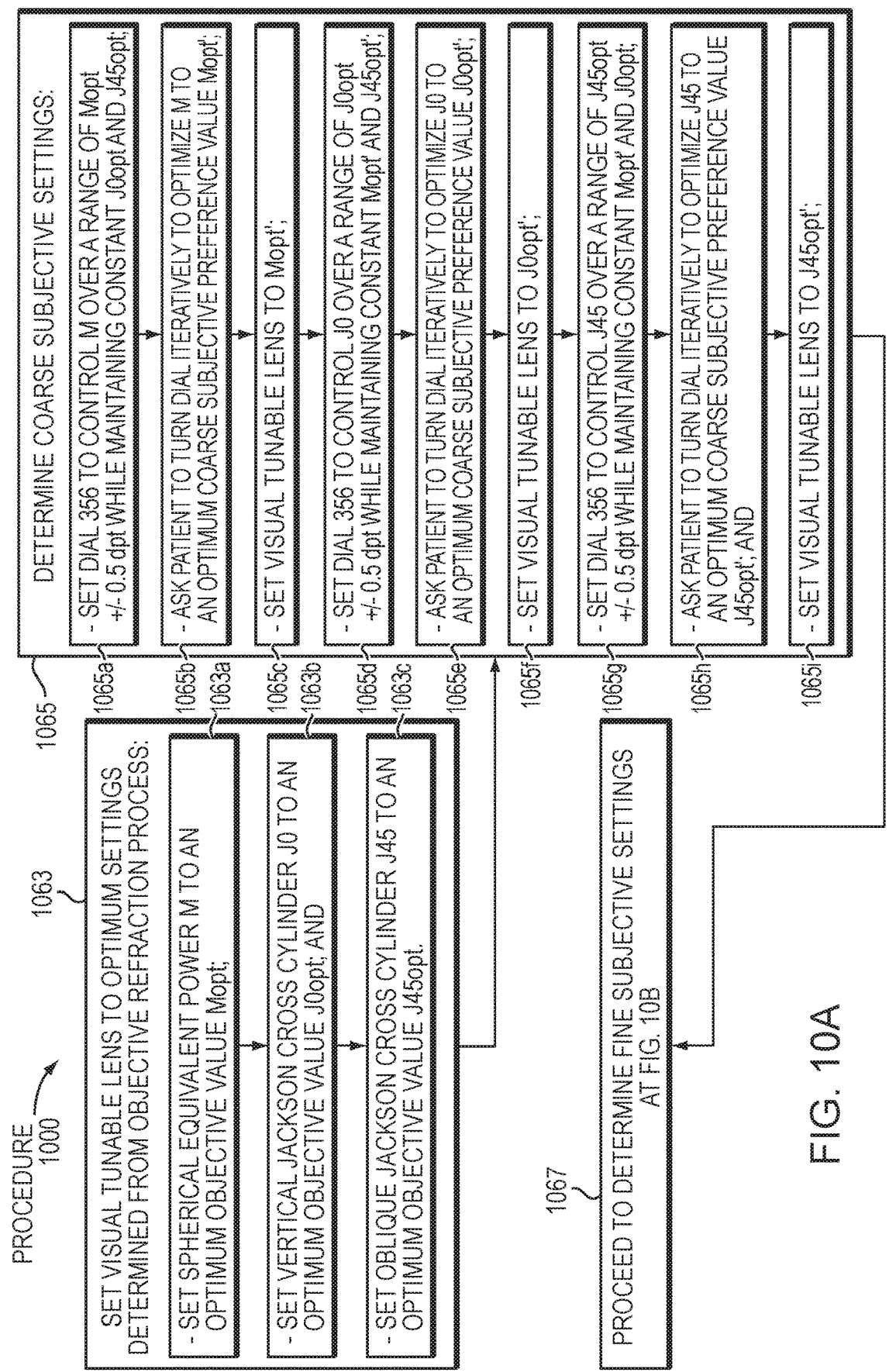

Self-usable embodiments are made possible in part because the eye can be aligned with the optics of the device via an external or internal fixation target, or visual or audio cues from the device, or both. Self-usable embodiments can be further enabled by automated or semiautomated operation of embodiment apparatuses and interactive instruction to a patient and saving settings made by a patient. FIGS. 10A-10B, as described hereinafter, provide one example of such an interactive procedure consistent with some embodiment apparatuses. However, embodiments disclosed herein may also be modified and used advantageously with clinician assistance to obtain results that are similarly unachievable by other handheld units and further unachievable unachievable by using mutually separate phoroptry and aberrometry instruments.

Thus, integrated autorefraction and phoropter functions allow the phoropter core (the tunable lens) to be automatically updated based on the autorefraction wavefront data. Furthermore, when the tunable lens is appropriately situated in or on the device incorporating the wavefront sensor, the tunable lens can serve as an eyeglass simulation to allow a patient to see through a lens at the appropriate location for an eyeglass with the final, proposed correction prescription implemented. Moreover, certain embodiments can be used to take advantage of the tunable lens to measure accommodation and presbyopia, as well as to perform lensometer functions by measuring optical parameters for a set of eyeglasses already owned by the patient or to be offered to the patient, for example. Furthermore, the lenses to be measured using embodiment devices may be lens blanks as well. An optician may want to locate the optical center position and confirm the power of the lenses before cutting the lens blanks to fit an eyeglass frame, for example.

Embodiment devices are preferably "open view," meaning that the patient can see through the device to a distant target to relax any accommodation of the eye. An embodiment apparatus can be designed to measure the aberrations of the user's eye in an unaccommodated state (i.e. the eye is relaxed and focused at infinity). A viewing target may be located at effective optical infinity, about 20 feet from the patient's eye. Viewing targets can include a standard eye chart, a spot of light produced by a target light source on the device, or another object in the surrounding environment. Such open view designs can reduce or eliminate the need for cycloplegic drops, and fogging may also be rendered unnecessary or optional.

By using a relatively low-cost, electronically tunable lens system, expensive approaches such as adaptive optics can be avoided. Embodiment devices can also be more mechanically robust and easier to handle and transport than systems having a set of physical lenses included in a phoropter, for example. A standard phoropter-style or trial frame lens system requires lens switching, which can result in fluctuations of the patient's eye and mechanical disturbances to the wavefront sensor apparatus.

It is noteworthy that available tunable lenses may have lower optical quality than fixed lenses typically used in high-quality optical systems for eye care. For this reason, optical engineers and eye care professionals would not generally be inclined to consider using a tunable lens in a system designed for high-quality eye examination, whether a phoropter or a wavefront aberrometer. However, the inventors have recognized that, where a device is designed for a tunable lens to work in combination with a wavefront sensor, the quality of wavefront aberrometry can be maintained and even enhanced due to iterative wavefront measurements in the presence of automatic, closed-loop, wavefront error cancellation by the tunable lens. Embodiments can provide wavefront measurements that are captured and processed continuously, such as at video rates, for example. Furthermore, a wavefront sensor apparatus can be calibrated with respect to any wavefront error caused by a tunable lens, thus enabling measurement of even high-order wavefront errors of a patient's eye with high accuracy. Furthermore, as noted hereinabove, a tunable lens also enables fast automated or semi-automated phoropter, lensometer, and accommodation measurement functions on the same device that is used for wavefront aberrometry, even with a portable, handheld device, and even when testing is self-administered by the patient.

Embodiments can provide a complete refraction system that enables refractive measurements to be performed anywhere by a minimally-trained technician or even by the subject patient himself or herself. This has significant global health and industrial utility.

FIG. 1 is a schematic block diagram illustrating an embodiment apparatus 100 for determining a property of an eye 106. The apparatus 100 includes a housing 102 having a port 105 configured to receive the eye 106 and to receive light 108 from the eye. The port 105 is "configured to receive" the eye 106 in the sense that the eye 106 can be placed near enough to, or in contact with, one or more portions of the port such that the light 108 from the eye can be received through the port 105. Thus, while the eye 106 is not required to be in contact with the port 105, in various embodiments, the eye 106 is an eye of a person whose forehead and cheek are placed against an eyecup 104 for registration and mechanical fixation with respect to the port 105. As a further example, another embodiment device having an eyecup configured to come into contact with a person's forehead and cheek is described hereinafter in connection with FIGS. 5A-5C. Some embodiments defining a binocular configuration may include two ports, also referred to herein as "first" and "second" ports, that include similar configurations and provide for similar functionalities for first and second respective eyes of a patient, as described in connection with FIGS. 5A-5C, for example.

The apparatus 100 in FIG. 1 also includes a visual tunable lens 110 mounted to the housing as part of the port 105. The visual tunable lens 110 is designated "visual" because it is possible for the eye 106 to see through the visual tunable lens 110. The visual tunable lens 110 is also configured to focus or defocus light received from the eye 106 to be passed via an optical path 112 to a wavefront sensor 116, which measures a wavefront of the light 108 from the eye. The "visual" tunable lens 110 is also closer to the eye 106, when the apparatus 100 is in use than an optional "light source tunable lens" that will be described in connection with FIG. 2, and which can be a similar tunable lens at a different location in the apparatus. In various embodiments, the visual tunable lens 110 mounted in the apparatus such that it is relatively close to the eye 106 when the apparatus is brought into proximity with the eye for examination. A smaller relative separation between the tunable lens and the eye can result in the tunable being smaller and less expensive than would otherwise be needed.

The visual tunable lens 110 has a focal length f and an optical power $P=1/f$ that are variable. In some embodiments, the visual tunable lens 110 is configured to apply a variable spherical power (focus/defocus) to the light 108 from the eye. In other embodiments, the visual tunable lens 110 can also apply astigmatic power (cylinder) and also vary axis of the cylindrical (astigmatic) power applied to the light. In some embodiments, the visual tunable lens can be configured to apply variable spherical and astigmatic optical powers, as well as apply axis orientation for the astigmatic power, mutually independently. In some embodiments, the visual tunable lens 110 is further configured to apply a spherical equivalent power, vertical Jackson cross cylinder, and oblique Jackson cross cylinder mutually independently.

It should be understood that any "tunable lens," as used herein, can include a plurality of individual tunable lenses arranged (optically stacked) in series, along the same optical axis, for example. Individual tunable lenses can be stacked in series (along the same optical axis) in order to increase the range of lens powers that can be simulated by the system. Stacking of tunable lenses may also improve the dynamic range or reduce the overall aberrations of the system. For example, a visual tunable lens may include a first individual tunable lens with a wide range of coarse tunability for a given optical correction such as sphere, as well as a second individual tunable lens with a narrow range of fine tunability for the given optical correction. Further, the optional mutual independence of spherical and astigmatic powers with variable axis may be achieved by applying the powers and axis using respective individual tunable lenses. This same method of using individual tunable lenses can be used to apply spherical equivalent power, vertical Jackson cross cylinder, and oblique Jackson cross cylinder mutually independently.

In some embodiments, the visual tunable lens 110 can be at least one of a liquid-filled lens, an electro-wetting lens, an Alvarez lens, spatial light modulator, deformable mirror, a lens with power that varies spatially (e.g., a progressive lens), a multi-lens system that changes lens distances to tune optical power (e.g., optical trombone, Badal system), or a tunable Fresnel lens. In some embodiments, the visual tunable lens can include a two-element object configured to apply the variable focal power as a function of lateral or rotational displacement of the two elements with respect to each other. For example, an Alvarez lens pair can include two such optical elements configured to be laterally displaced with respect to each other, in a direction perpendicular to an optical axis of the elements, to apply the variable focal power. Another embodiment includes a lens that is tunable by virtue of being asymmetrical having different focal powers along different points on the lens. Such an asymmetrical lens can be displaced along a plane perpendicular to an optical axis of the system in order to vary the focal power of the lens. Asymmetrical lenses of this type have been termed "hybrid Fresnel lenses" and have been used in virtual reality headsets, for example.

Example tunable lenses that can be used in embodiments described herein can include, for example, the Optotune® EL-10-30 series of liquid-filled tunable lenses. This series has focal lengths and corresponding optical powers that can be tuned within milliseconds, providing fast response for iterative wavefront measurements performed in a closed loop fashion, as further described hereinafter. One model of the Optotune® EL-10-30 can be tuned between +8.3 and +20 diopters (dpt) of optical power, corresponding to +120 to +50 mm in focal length, for example. Furthermore, the Optotune® EL-10-30 series is available with near-infrared (NIR) optimization, which is useful for detecting NIR light received from the eye, as is preferably done in some embodiments. Tunable lenses can also cover negative power ranges to be used with myopic patients. The Optotune® EL-10-30-C-NIR-LD-MV, for example, can be tuned between −1.5 and +3.5 dpt. Another example tunable lens that can be used includes the Varioptic Visayan® 80S0 electro-wetting tunable lens, which can apply variable focus (−12 to +12) and astigmatism (−6 to +0 dpt) powers.

In FIG. 1, the visual tunable lens 110 is also configured to pass the light 108 from the eye along the optical path 112 toward the wavefront sensor 116. The wavefront sensor 116 is configured to receive the light from the eye and to measure a wavefront 114 of the light 108 from the eye. The wavefront sensor 116 can be, for example, a Hartmann-Shack wavefront sensor comprising an array of lenslets having the same focal length and configured to focus light received, at various points in a cross-section of a beam of light, onto a photon sensor, which can be a CCD or CMOS array, for example. As is known and understood in the art of wavefront sensing, such a wavefront sensor produces a pattern of spots, from which a wavefront of the light being measured can be determined with high precision.

The wavefront sensor 116 provides a representation 118 of the wavefront of the light 108 to a determination module 120. The representation 118 of the wavefront can include, for example, an image in the form of pixel values for a sensor array of the wavefront sensor 116. However, in other embodiments, the wavefront sensor 116 can be configured to provide the representation 118 in other forms, such as a compressed image or a series of spot separations or spot center positions on the sensor array, for example.

The determination module 120 is configured to determine a property 122 of the eye 106 based on the measured wavefront from the sensor 116. The property 122 can include an optical property such as one or more values for aberrations of the eye, an eyeglass or contact lens prescription for the eye, objectively or subjectively determined correction parameters, accommodation amplitude or presbyoptic prescription, lensometer data for eyeglasses worn or intended to be worn by a patient, or other related data. Moreover, in some embodiments, the determination module 120 can be configured to output other data, such as a spot pattern produced by the wavefront sensor 116. Such spot patterns can be used advantageously in some embodiments to provide live images for alignment of the eye and other purposes, as described further hereinafter.

In some embodiments, the housing 102 is configured to be gripped by at least one hand of the person having the eye 106 to support a full weight of the apparatus during use. An example of such a configuration is included in FIGS. 5A-5C, for example. These embodiments can enable a person having the eye to use the apparatus 100 portably, even in the absence of a doctor, operator, or other assistance to obtain eye data such as a prescription for eyeglasses.

In some embodiments, the port 105 can include an optical window in the housing 102 or can be an opening in a modular attachment to the housing. In some embodiments, the eyecup 104, the visual tunable lens 110, and the port 105 can be physically separate. In some embodiments, port 105 can be described as a "proximal" port, and an additional "distal" port can also be provided in the housing, such that the device is "open view," enabling the eye 106 to see all the way through the apparatus 100 to an object or feature external to the apparatus 100. The apparatus 100 is monocular, in the sense that it is configured to receive one eye. However, in other embodiments, an apparatus can be binocular, as described hereinafter in connection with FIGS. 5A-5C, for example. In some binocular configurations, a second visual tunable lens can be configured to be mounted to the housing and to apply a variable focal power to light from the second eye. The second visual tunable lens can perform functions similar to those of the first visual tunable lens 110, or separate functions, as will be described further hereinafter.

In some embodiments, an apparatus can include a visual tunable lens configured to be adjusted iteratively to optimize the wavefront 114. For example, the visual tunable lens 110 can be adjusted to make the wavefront 114 as close as possible to a plane wavefront, such that aberrations produced by the eye 106 can be minimized, and the visual tunable lens 110 can simulate an eyeglass lens worn by a person having the eye 106.

In some embodiments, the eye 106 is a living eye of a person. However, in other embodiments, the eye 106 is an artificial eye that can be used for calibration purposes, for example, or for determining the prescription of a pair of eyeglasses in accordance with lensometer functions, as further described hereinafter in connection with FIGS. 5A-5C.

Figure 2:
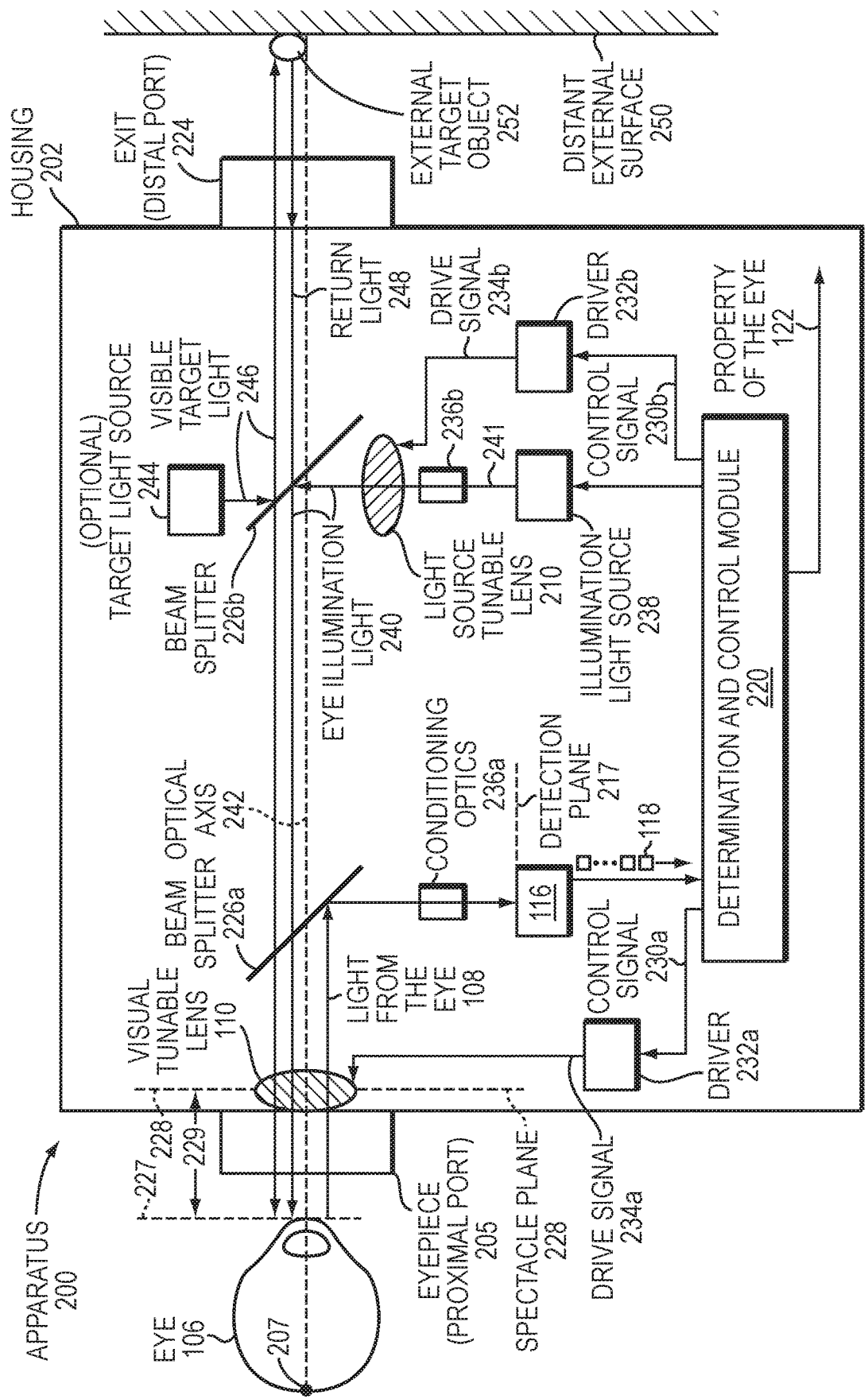
FIG. 2 is a schematic block diagram illustrating an alternative embodiment apparatus that is open view and also includes other optional features.

FIG. 2 is a schematic block diagram illustrating an embodiment apparatus 200 that is configured to be open view and also include other optional features. Open view embodiments have the advantage that the eye 106 can view target indicia external to, and spaced away from, a housing 202 of the apparatus 200 through a visual channel between two sides of the apparatus, as further described hereinafter. Provided an external target object 252 at a distant external surface 250, or other target indicia, are spaced away from the eye 106 at effective infinity (greater than or equal to 20 feet from the eye), the eye 106 can remain substantially unaccommodated and relaxed, such that refractive measurements performed by the apparatus 200 can be improved. It has been shown that wavefront aberrometry with a closed view configuration induces more instrument myopia (0.3 dpt) compared to an open view system (e.g., A. Cervino et al., Journal of Refractive Surgery, 2006).

The apparatus 200 is configured to have the visual tunable lens 110 mounted within close proximity to an eyepiece 205 serving as a proximal port configured to receive the light 108 from the eye 106 through the housing 202. The eyepiece 205 is detachable from the housing 202, such that it is modular and can allow the housing 202 to receive other modular attachments. Example modular attachments can include a lensometer attachment, as described hereinafter in connection with FIGS. 5A-5C, a calibration attachment, as described hereinafter in connection with FIGS. 5D-5K, or other eyepieces having different focal ranges.

As is known, different eyes can have widely varying optical aberrations and require widely varying prescriptions.

A given visual tunable lens having a given tunability range, such as the Varioptic Visayan® 80S0 tunable lens described hereinabove, which has an adjustment range from −12 to +12 dpt, will be able to simulate eyeglass corrections for patients having a given range of needed correction. Thus, in some embodiments, the eyepiece 205 with the visual tunable lens 110 covering one range of corrections can be modularly replaced with another eyepiece having a different tunable lens covering a different range of corrections to address patients having a correspondingly different range of correction.

Alternatively, in some embodiments, the eyepiece 205 is configured to accommodate additional lenses and optics for various purposes. For example, the eyepiece 205 can be configured to accommodate a fixed lens, also attached to the housing, to apply a fixed focal power to the light 108 from the eye to shift a range of refractive correction measurement of the apparatus 200. Furthermore, a variety of fixed lenses having various fixed focal powers can be alternately received by the eyepiece 205, or by another portion of the housing 202, or inside the apparatus 200, for example, to address different persons with different refractive corrections. Furthermore, the eyepiece 205 can also be configured to accommodate a fogging lens or optic configured to fog the view of the eye through the apparatus 200. Fogging has the advantage that it is a non-cycloplegic (does not require cycloplegia) approach and also avoids the need for an open view system. Fogging can also be modified according to a given patient's type of refractive error (myopia or hyperopia).

Still further, the eyepiece 205 can be configured to accommodate a visual tunable lens that comprises a series of individual tunable lenses as described hereinabove in relation to FIG. 1. Using a series of individual tunable lenses instead of a single visual tunable lens, for example, may increase the range of lens powers that can be simulated by the system. A series of individual tunable lenses may also improve the dynamic range or reduce the overall optical aberrations of the system. The individual tunable lenses may be arranged (stacked) optically in series with each other, all centered on a common optical axis, for example. The individual tunable lenses may be used to cover separate larger and smaller optical correction ranges, for example. Further, individual tunable lenses in such an arrangement (stack) may be configured to address, separately, different respective optical corrections. A series of individual tunable lenses can separately address spherical power, astigmatic power (cylinder), axis of the cylindrical (astigmatic) power applied to the light, and even aberrations of higher optical order mutually independently, for example. In some embodiments, the series of individual tunable lenses can be configured to apply a spherical equivalent power, vertical Jackson cross cylinder, oblique Jackson cross cylinder, and higher-order corrections mutually independently.

As is understood in the science of refractive care, corrective lenses of eyeglasses are typically situated about 14 mm from the surface of the cornea of a patient's eye. In preferred embodiments, in order to best simulate refractive correction of eyeglasses, the visual tunable lens 110 is configured such that a plane 228 of the lens 110 is configured to be a distance 229 of about 14 mm from a front surface 227 of the cornea. Thus, the plane 228 at which the visual tunable lens 110 is situated, in this case, corresponds to the spectacle plane for the eye 106 when the proximal port has received the eye.

While a refractive measurement is being performed, the eye 106 can see light 248 from the external target object 252 located on the surface 250 at effective infinity. This open view design is facilitated by two beam splitters 226a and 226b that perform various functions within the apparatus and are also largely transparent in the visible spectrum perceived by the eye 106.

The beam splitter 226a is configured to reflect NIR light 108 received from the eye 106 toward the wavefront sensor 116. The optical path between the beam splitter 226a and the wavefront sensor 116 also includes various conditioning optics 236a. The conditioning optics 236a can include, for example, a beam aperture/iris, a narrowband optical filter configured to pass only NIR light of a given wavelength, an attenuation filter, etc. The conditioning optics 236a can also optionally include cross-polarizers disposed in the optical path and configured to minimize unwanted light at the wavefront sensor 116. In the case of a beam aperture, light from the eye illumination light source can be restricted by the aperture, and example aperture sizes may range between about 50 μm and about 500 μm.

The wavefront sensor 116 provides the wavefront representation 118 to a determination and control module 220, which is configured to determine the property 122 of the eye. The determination and control module 220 performs functions similar to those of determination module 120 in FIG. 1, but the module 220 also includes control functions. In particular, the control module 220 outputs a control signal 230a to a lens driver 232a, which outputs a drive signal 234a to the visual tunable lens 110 to set the lens 110 to the appropriate focal power. With appropriate logic in the determination and control module 220, this forms a closed-loop system (circuit), wherein the wavefront representation 118 can be continuously monitored, and wherein the control module 220 can provide appropriate control signals 230a to update the setting of the visual tunable lens 110 continuously. This process can be iterative to minimize wavefront errors of the eye 106 using the visual tunable lens 110. In this manner, the variable focal power of the visual tunable lens may be adjusted iteratively in response to successive wavefront measurements in order to minimize a wavefront error of the light from the eye. Various iterative processes are further described hereinafter in connection with FIGS. 6 and 10A-10B, for example.

The apparatus 200 also includes an illumination light source 238 that is configured to output NIR light (eye illumination light 240) toward the eye. In other embodiments, the eye illumination light and light received from the eye may be visible or infrared. The illumination light 240 is reflected by the beam splitter 226b, passes through the beam splitter 226a, and exits the proximal port 205 through the visual tunable lens 110 to enter the eye 106. The light 240 is intended to form a focused spot 207 at the retina of the eye 106. A portion of the eye illumination light 240 is reflected and scattered by the eye 106 and is received as light 108 from the eye to be detected at the wavefront sensor 116.

When the eye illumination light 240 passes through the visual tunable lens 110, its convergence or divergence is affected by the setting of the tunable lens 110. In order to maintain a focused spot 207 at the retina, the apparatus 200 includes a light source tunable lens 200 that applies variable focal power to the eye illumination light 240 to maintain the focused spot 207 at the retina. Thus, when the determination and control module 220 adjusts the focal power of the visual tunable lens 110, the light source tunable lens 210 can be adjusted to a corresponding value that affects only the eye illumination light 240 and maintains the focused spot 207. As will be understood by those skilled in the art of optics, the corresponding settings between the visual tunable lens and the light source tunable lens 210 can be pre-calibrated such that an appropriate setting for the lens 210 can be known for every setting of the tunable lens 110. In order to make these corresponding adjustments, the determination and control module 220 can store calibration data or receive the calibration data from another source, such as memory illustrated in FIG. 4, to make the appropriate corresponding settings.

In cases in which the visual tunable lens 110 can correct over the refractive error range needed for a given patient, corresponding adjustments to the light source tunable lens 210 may not be required. However, the light source tunable lens 210 can be used to extend the range of measurement for a given visual tunable lens 110 by reducing spot size of illumination light focused onto the retina of the eye, particularly in case the eye has a refractive error greater in magnitude than the maximum refractive error that can be corrected with the visual tunable lens 110. Furthermore, the light source tunable lens 110 can be used to expedite analysis of a patient's eye and determination of a corresponding prescription by sweeping the range before, during, or after tuning the visual tunable lens. For example, if a particular visual tunable lens cannot be tuned as fast as desired for a given set of refractive measurements, then the optical power of the light source tunable lens may be adjusted, in parallel with the optical power of the visual tunable lens, to achieve a particular combined power setting more quickly. Moreover, the light source tunable lens 210 can be used to reduce speckle, as described further hereinafter.

In order to control the light source tunable lens 210 in FIG. 2, the determination and control module 220 outputs a control signal 230b to a lens driver 232b. The driver 232b outputs a drive signal 234b to the light source tunable lens 210 to make the appropriate setting. Preferably, where the visual tunable lens 110 controls sphere, cylinder, and axis independently, the light source tunable lens 210 includes similar, independent adjustments such that the eye illumination light can remain focused on the retina for all visual tunable lens settings.

The optical path between the illumination light source 238 and the beam splitter 226b also includes conditioning optics 236b. The optics 236b can include some functions similar to those of the conditioning optics 236a. For example, the optics 236b can include a narrowband filter configured to pass only light of wavelengths corresponding to the illumination light source 238. The optics 236b can also include an iris (aperture) configured to adjust diameter of the eye illumination light 240 or a diaphragm to define the illumination light and to align the light 240 with the beam splitter 226b. The illumination light source 238 can be a light emitting diode (LED), but it can also be a diode laser or other collimated, coherent (or semi-coherent, such as a superluminescent diode) light source, for example.

As will be understood by those skilled in the art of optics, a coherent illumination light source 238, such as a laser, can produce some degree of speckle pattern at the eye 106 and at the wavefront sensor 116, depending on the degree of coherence of the light source 238. Random speckle patterns with high contrast may, therefore, be present in a spot diagram produced using the wavefront sensor. These speckle patterns can interfere with the ability of the wavefront sensor 116 to distinguish sensitively between laser speckle and the spot pattern that defines the wavefront of the light 108. Speckle contrast can reduce the accuracy of localizing each spot in a detected spot diagram, which, in turn can reduce the accuracy of a wavefront that is reconstructed using the detected spot diagram.

One advantage of embodiments is that the determination and control module 220 can be configured to dither (i.e., rapidly apply variable focal power or adjust another refractive setting of) either the visual tunable lens 110, the light source tunable lens 210, or both tunable lenses slightly while spot diagrams are being acquired by the wavefront sensor. In the case of the light source tunable lens being dithered, variable focal power is applied to the light 241 from the light source 210. This dithering can randomize the speckle pattern produced by the eye illumination light 240 at the eye 106, or, equivalently, randomize a speckle pattern produced by the light 108 from the eye at the wavefront sensor 116. This dithering, as described in connection with FIG. 9B, for example, can introduce small variations into the wavefront of the light to randomize the speckle pattern generated at the eye by an eye illumination light source and received at the wavefront sensor.

Such dithering can reduce or eliminate the effects of laser speckle pattern that would otherwise diminish measurement sensitivity of the wavefront sensor 116. If the magnitude of the dithering is sufficiently large, the speckle pattern will be randomized over the course of an acquisition. If the speckle pattern is sufficiently randomized over the course of a single exposure, an averaged-out speckle pattern will be captured. This implies that the spots in the spot diagram can be more accurately localized due to the reduced speckle contrast. Furthermore, a dithering magnitude that is sufficiently large to randomize the speckle pattern can also be small enough to have no appreciable impact on the size of the focal spot 207 or the accuracy of the wavefront measurements. An example spherical dithering magnitude includes, for example, +/−0.01 dpt. However, other example spherical dithering magnitudes are much greater, such as in a range of 0.25-0.5 dpt, for example. Other tunable lens parameters, such as cylinder power, axis, higher order parameters, or parameters such as spherical equivalent power in other known basis sets, for example, may be dithered as an alternative to, or in addition to, dithering sphere. Thus, the ability to eliminate or reduce laser speckle noise is yet another advantage of tunable lenses used in embodiment apparatus and methods.

The apparatus 200 also includes an optional target light source 244 mounted to the housing 202. FIG. 2 illustrates the target light source mounted inside the housing 202, but other embodiments can include outside mounting. The target light source 244 is configured to output visible target light 246, which is reflected by the beam splitter 226b and output from the apparatus 200 through a distal port 224 in the housing. Together, the proximal and distal ports form a visual channel parallel to the optical axis 242 through which the eye 106 can see the external target 252. The visible target light 246 creates a spot or other indicia on the distant external surface 250 external to and spaced away from the housing 202. The spot or other indicia can be viewed by the eye 106 to cause the eye to be unaccommodated, with the distant external surface 250 at effective infinity from the eye. The visible target light 246 is reflected or scattered from the surface 250, and a portion returns to the eye 106 as return light 248 through the apparatus 200. However, in other embodiments, the target light source 244 is not used. Instead, the return light 248 viewed by the eye 106 is ambient light scattered or reflected from the external target object 252 and through the apparatus 200.

In the schematic block diagram illustrated in FIG. 2, the light 108 from the eye, visible target light 246, return light 248, and eye illumination light 240 are shown as being offset from the optical axis 242 of the eye. This depiction is for convenience in illustration only, and all of these light beams can be mutually coincident, collinear, and centered on the optical axis 242.

However, in preferred embodiments, the eye illumination light 240 exiting the port 205, and the light 108 from the eye entering the port and received by the tunable lens 110, are non-collinear. This non-collinear orientation can reduce or eliminate eye illumination light 240 that is back-reflected from the surface of the cornea of the eye from being received at the wavefront sensor. This can be very helpful in reducing noise and increasing signal-to-noise ratio for wavefront signals detected by the wavefront sensor.

In conformity with the principle of making the light entering the eye non-collinear with the light exiting the eye, various adjustments can be made to the optical configuration in FIG. 2. For example, a detection plane 217 of the wavefront sensor 116 can be non-perpendicular to an illumination axis 241 of the illumination light source 238. The wavefront sensor 116 can be slightly non-parallel with the optical axis 242 of the eye. In other words, the detection plane 217 of the wavefront sensor can be non-parallel with an illumination axis of the eye illumination light 240 within an optical path between the beam splitter 226b and the eye 106, and the detection plane 217 can be non-perpendicular with an axis of illumination of the eye illumination light 240 within an optical path between the eye illumination light source 238 and the beamsplitter 226b.

Figure 3:
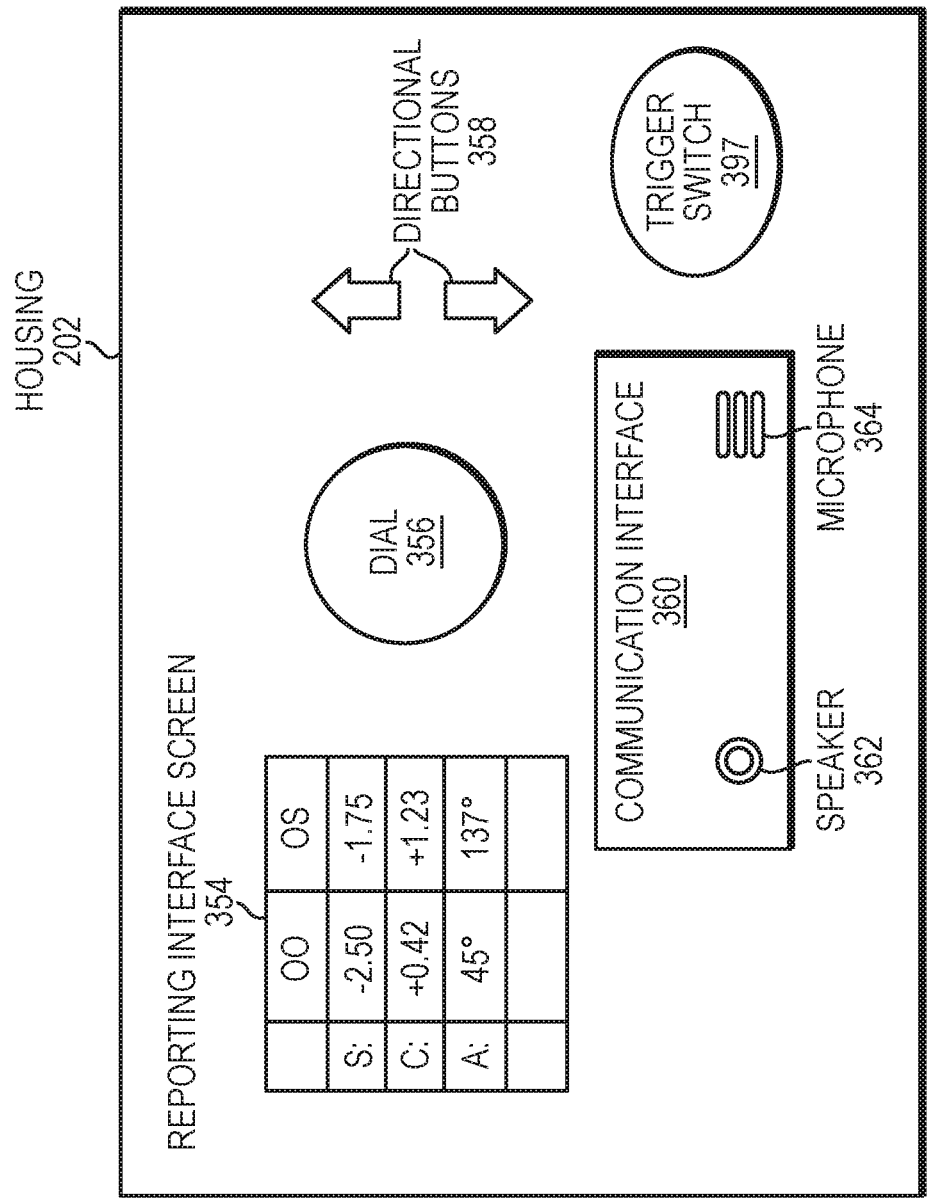
FIG. 3 is a schematic diagram illustrating various optional input and output features of embodiment devices, such as those illustrated in FIGS. 1-2.
Figure 4:
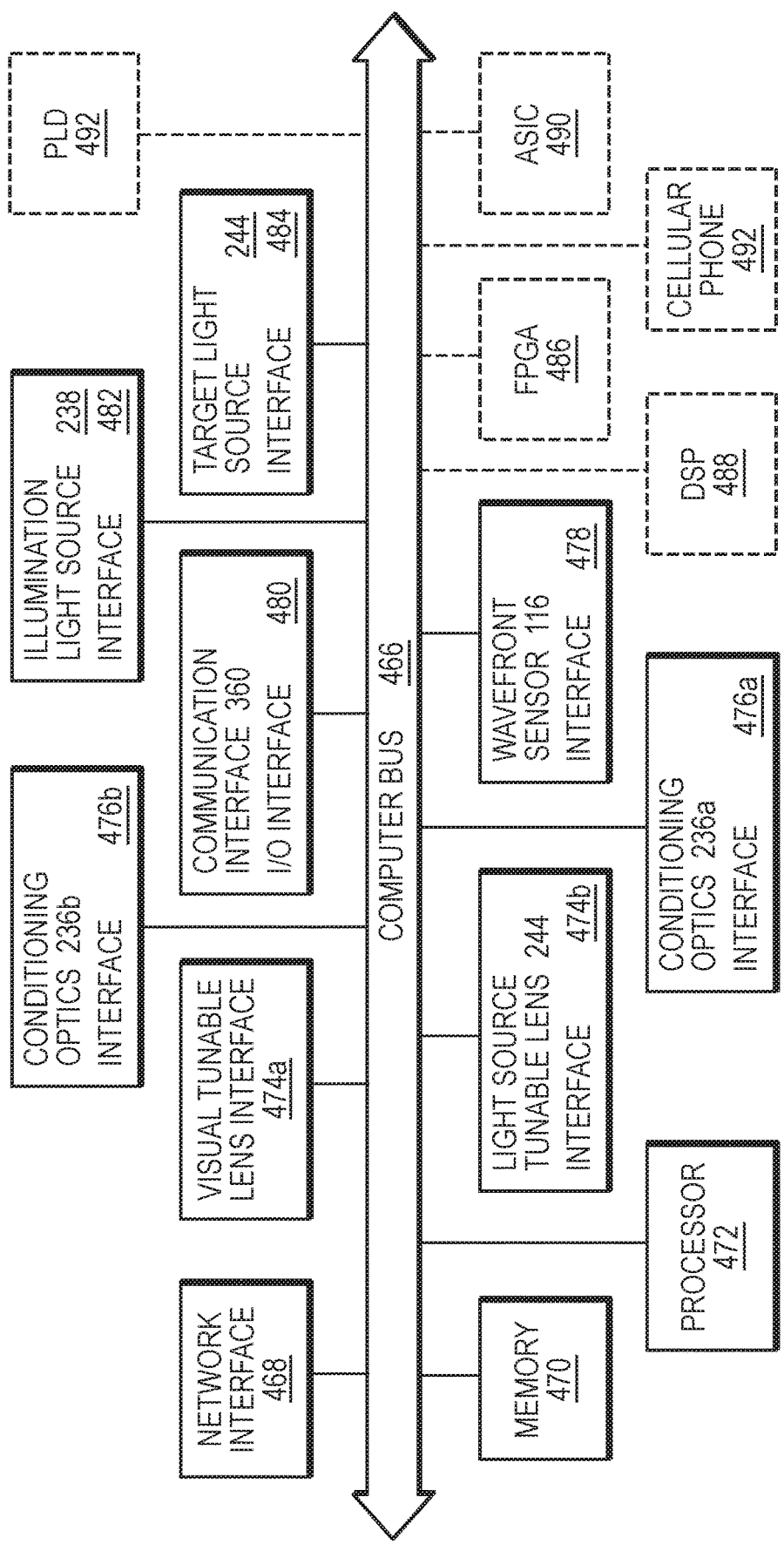
FIG. 4 is a computer interconnect diagram illustrating various components of the determination and control module in FIG. 2 and its connections to various components, including some components illustrated in FIG. 2, some optional components shown in FIG. 3, as well as some that are not illustrated in FIGS. 2-3.

FIG. 3 is a schematic diagram illustrating various optional input and output features of embodiment devices, such as those illustrated in FIGS. 1 and 2. In particular, the housing 202 of the apparatus 200 illustrated in FIG. 2 can include a reporting interface screen 354, a dial 356, a communication interface 360, directional buttons 358, and a trigger switch 397. The dial, directional buttons, and trigger switch are examples of manual controls that can be configured to be adjustable by an eye patient, or by a clinician, to adjust the variable focal power of the visual tunable lens in accordance with a subjective refractive preference of the eye patient. In other embodiments, these inputs and outputs are provided by peripheral devices in operational communication with the apparatus 200. Examples of peripheral devices, can include a cellular phone, as illustrated in FIG. 4, or a separate, handheld, wired or wirelessly connected controller that a clinician, patient or other user can use to specify inputs or receive outputs, for example.

Figure 5A:
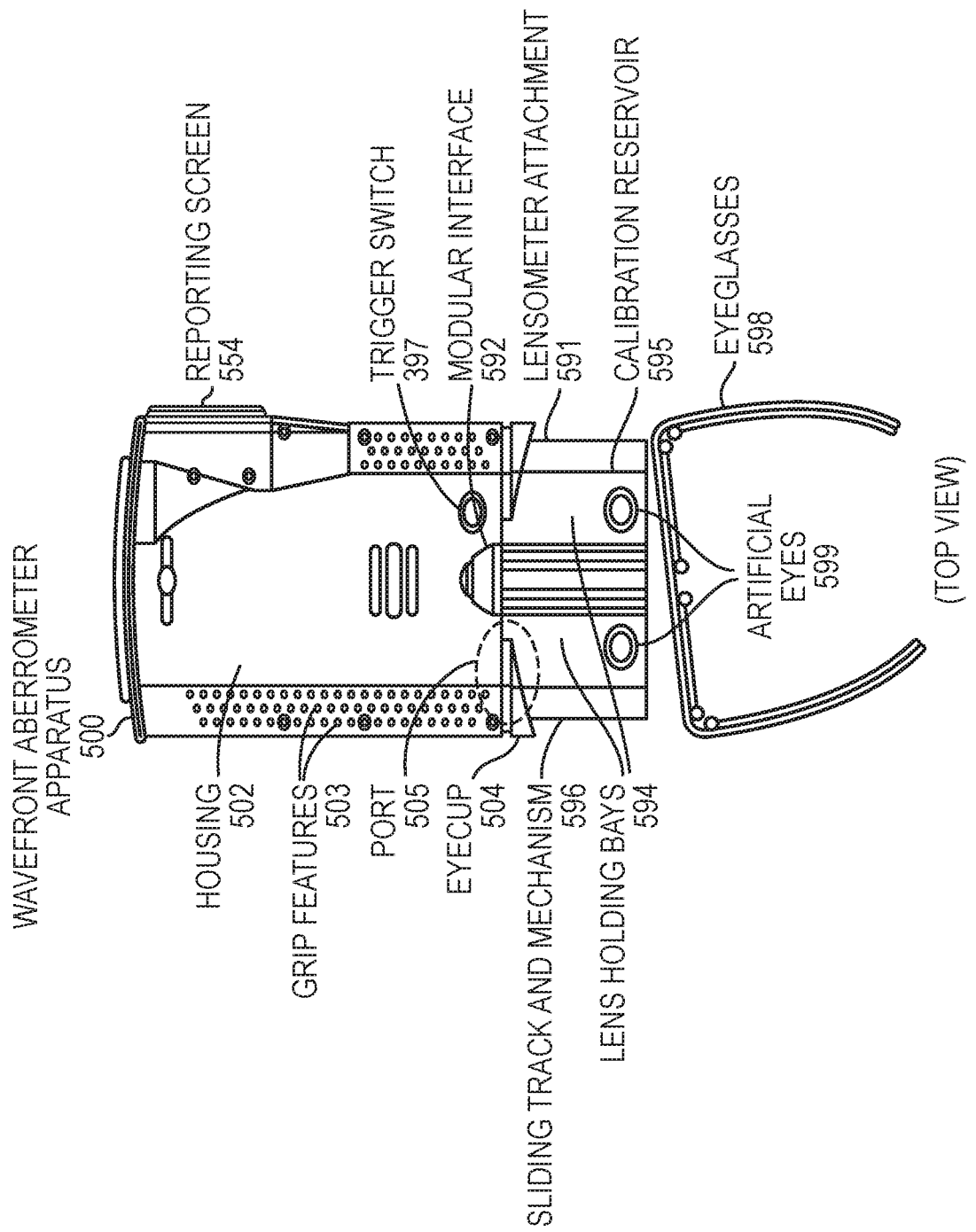
FIG. 5A is a top-view illustration of an embodiment, binocular, wavefront aberrometer autorefractor apparatus with a lensometer module attached; the apparatus of FIG. 5A is also referred to as "QuickSee" apparatus herein).

The reporting interface 354 can be an LCD screen, for example, on the housing 202 that can be read by a user to obtain a prescription for eyeglasses, as illustrated, or another property of the eye 106. The reporting interface screen 354 provides sphere (S), cylinder (C), and axis (A) measurements for right (OD) and left (OS) eyes after measurements are completed. Various other information can also be presented to a user or operator using the reporting interface screen 354, such as information about higher order aberrations, Zernike polynomial parameters measured for the right and left eyes, a contact lens prescription, alignment information, and other information. As another example, the reporting interface screen 354 can show a live image produced by the wavefront sensor 116 in FIG. 2 to assist with calibration of the apparatus or for eye alignment purposes for initial setup, for example. Further alternative information that can be provided by the reporting interface screen 354 includes static images produced by the wavefront sensor 116, other information representative of the wavefront detected, calibration instructions, operating instructions, etc. Furthermore, in some embodiments, the reporting interface screen 354 is a touchscreen enabling a user to input information, such as selecting a measurement to be performed. Actual placement of the features shown in FIG. 3 onto a device housing or peripheral module may vary in various embodiments. An example placement of the trigger switch 397 is illustrated in FIGS. 5A-5C.

The communication interface 360 includes a speaker 362 configured to provide audible instructions to a user, such as instructions for how to align the eye to an input port of the housing for best measurement accuracy. In some embodiments, the speaker 362 provides step-by-step instructions to the user before and during a measurement of the eye. The interface 360 also includes a microphone 364 that can be used to receive inputs from the user, such as a refractive preference of the user. This feature is particularly useful when the apparatus 200 operates in phoropter mode, as will be described further hereinafter in connection with FIGS. 8A-8B, for example. Thus, the speaker 362 can provide certain instructions such as "tell me which lens setting is best, one or two." The apparatus 200 illustrated in FIG. 2 can then set the visual tunable lens to two different settings, one subsequent to the other, and the speaker 362 can indicate which setting is 1 in which setting is 2. A user can then speak, through the microphone 364, "one" or "two" to indicate which setting of the visual tunable lens 110, simulating an eyeglass correction, is preferable to the user, who is the person whose eye 106 is being measured.

As an alternative to the verbal communication just described for specifying subjective preferences, the directional buttons 358 can be pressed by a user to specify which visual tunable lens 110 setting is preferable. For example, the wavefront sensor 116 can be used to determine an objective refractive correction for the user. The visual tunable lens 110 can then be set to simulate a corrective lens applied to the eye 106. The user can then be given the opportunity to specify various changes to refractive settings of the visual tunable lens 110, using the directional buttons 358, in accordance with a subjective preference. This range of adjustment can be a fine adjustment over a relatively small range, such as a spherical correction adjustment range of +/−0.25-0.50 dpt. Once the user has specified spherical correction to the subjective preference, the buttons 358 can then be used to optimize cylinder and axis in turn according to subjective preferences, in a similar fashion. After the visual tunable lens 110 is set to all the preferred settings for sphere, cylinder, and axis, the process can be repeated iteratively for greater precision or to evaluate repeatability of subjective preference settings.

The dial 356 can be used as an alternative to the directional buttons 358. For example, the user can turn the dial 356 to adjust the spherical correction over the limited range of +/−0.25 dpt or +/−0.50 dpt, for example. The dial 356 can be preferable to the directional buttons 358 since rotational motion of the dial 356 can be smoother and cause less disturbance to the housing 202 than pressing buttons. The dial 356 may also be easier to use for other reasons, such as the user's ability to turn the dial 356 quickly or slowly, in accordance with the user's preference and the degree of adjustment required.

The trigger switch 397 provides another means of input by the user to the apparatus. In particular, as further described hereinafter in connection with FIG. 5A and FIGS. 8A-8B, for example, the trigger switch 397 can be pressed by the user when the user is ready for a measurement to occur, and then the user can release the trigger switch 397 once a simulated refractive correction provided by the visual tunable lens 110 operating in closed-loop fashion with the wavefront sensor is completely satisfactory. An example location for the trigger switch 397 is shown on the embodiment device illustrated in FIG. 5A.

FIG. 4 is a computer interconnect diagram illustrating various components of the determination and control module 220 in FIG. 2 and its connections to various components, including some internal components shown in FIG. 2 and other optional components shown in FIG. 3, as well as some other optional components that are not illustrated in FIGS. 2-3. In the apparatus embodiment illustrated in FIG. 2, the determination and control module 220 performs all necessary computing and control functions for the apparatus 200. It should be noted that in other embodiments, these functions can be distributed between a determination and control module and other processors or controllers, as will be understood by those skilled in electrical and computer engineering.

The determination and control module 220 includes a computer bus 466 used as an interconnect for various components. The module 220 includes memory 470 and a processor 472 that are used to store data and program instructions and perform necessary processing functions, processing functions can include determining the property of the eye, such as optical properties including a refractive correction prescription to be applied to the eye, based on the measured wavefront, the tunable lens setting, and any objective preference information obtained. The representations 118 of the wavefront entering the module 220 in FIG. 2 can be stored in the memory 470 for analysis by the processor 472. The module 220 also includes a network interface 468 coupled to the computer bus 466 for communicating with outside computers or networks if desirable. The network interface 468 can be used to report refractive results to an external computer or network for eyeglass ordering purposes, for example, or allow the functioning of the apparatus 200 to be monitored by an external or even remote computer, for example.

The processor 472 is coupled to a visual tunable lens interface 474a that controls the driver 232a illustrated in FIG. 2. Thus, through the visual tunable lens interface 474a, the processor 472 can control the settings for the visual tunable lens 110. In a similar fashion, the processor 472 is coupled to a light source tunable lens interface 474b for control of the light source tunable lens 210 illustrated in FIG. 2. It should be understood that, where either the visual tunable lens 110 or the light source tunable lens 210 includes a series of individual tunable lenses, as described hereinabove in relation to FIG. 1, either interface 474a or 474b may correspondingly include a series of individual interfaces for mutually independent control of the respective, individual tunable lenses.

The module 220 also includes interfaces 476a and 476b to control the conditioning optics 236a and 236b, respectively. The interfaces 476a-b are particularly useful in cases in which the conditioning optics are adjustable. For example, the conditioning optics 236a-b can include such features as variable attenuation and adjustable diaphragms and irises for beam conditioning.

The module 220 also includes a wavefront sensor interface 478 for receiving data from the wavefront sensor 116 in FIG. 2. A communication interface 480 in the module 220 allows the module 220 to communicate data to and from the communication interface 360 illustrated in FIG. 3. While not shown in FIG. 4, other interfaces can be provided in the determination and control module 220 for sending data to, and receiving data from, the reporting interface screen 354, dial 356, directional buttons 358, and trigger switch 397, which are illustrated in FIG. 3. Interfaces 482 and 484 are also included in the module 220 for controlling the illumination light source 238 and the target light source 244, respectively, which are illustrated in FIG. 2. For example, these light sources may be turned off when not in use, and their intensity may also be adjustable in certain embodiments.

The network interface 468 can include a wired or wireless interface, such as a universal serial bus (USB) interface, a wired Ethernet interface, a bluetooth communication module, a wireless infrared (IR) interface, a wireless local area network (WLAN) interface, or a wireless cellular data interface. Through such example interfaces, the processor 472 can communicate with an external or remote device that is outfitted with a similar communication interface. Such an interface can be used to print eye measurement results, store results on a thumb drive or other storage medium, send measurement results to a personal computer, cellular phone, smart phone, or cloud-based server, send prescription orders for eyeglass or contact lens prescriptions via any of these or other known means, communicate in other ways, or provide other output data. In one example, objective refraction results, subjective refraction results, lensometry results, accommodation measurements, another eye property, machine learning results, or a combination thereof, as determined by any one or more of the procedures illustrated in FIGS. 7, 8, 9A, 9C-9F, and 10A-10B, may be communicated directly or indirectly to a desired location or device with the network interface 468 being configured appropriately.

One or more of the interfaces illustrated in FIG. 4 can be replaced or have its functions augmented by a suitably programmed device, such as an optional field-programmable gate array (FPGA) 486 or a digital signal processor (DSP) 488. Furthermore, an application-specific integrated circuit (ASIC) 490 or programmable logic device (PLD) 492 can also be used.

As also illustrated in FIG. 4, the module 220 can include an interface used to communicate with a cellular phone 492. In some embodiments, the cellular phone can be configured to be attached to the housing 202 or can be otherwise programmed to perform some of the functions described in connection with FIG. 2 for the determination and control module 220. Furthermore, in some embodiments, the cellular phone 492 is used to display a representation of the wavefront of the light from the eye. Such a representation can be used for alignment of the eye to the apparatus 200 or for other subjective or objective analytical purposes, for example. In some embodiments, the cellular phone 492 can be used to perform the functions of the reporting interface screen 354 shown in FIG. 3, as well as other input or output functions of the dial 356, communication interface 360, directional buttons 358, or trigger switch 397. Furthermore, in some embodiments, the cellular phone can be used as a Hartmann-Shack wavefront sensor. For example, a standard multi-pixel sensor array on the cellular phone that is used to acquire photographs can be adapted to perform the functions of the light sensor array of the Hartmann-Shack wavefront sensor, and a separate lenslet array can be used to focus the light 108 received from the eye onto the sensor array. In some embodiments, the cellular phone includes two multi-pixel sensor arrays that are used as respective Hartmann-Shack wavefront sensors for respective eyes of a patient. Further, a first one of the two sensor arrays may be used as a wavefront sensor, while a second one of the two sensor arrays may be used to perform one or more of pupil measurements, karatometry, iris imaging, or other known ophthalmic imaging functions.

FIG. 5A is a top-view illustration of an embodiment, binocular, wavefront aberrometer apparatus 500. The apparatus 500 is particularly configured to enable not only wavefront aberrometer measurements using the visual tunable lens 110 as illustrated in FIG. 2, but also to enable lensometer measurement functions. The apparatus 500 includes a housing 502, which includes grip features 503 configured to be gripped by at least one hand of a person having the eye 106 to support a full weight of the apparatus 500 during use.

Connected to the housing 502 is an eyecup 504 configured to provide mechanical registration of the apparatus 500 against a forehead and cheek of a person (user, patient) having the eye 106. A port 505 in the housing is configured to receive the eye 106 and to receive light from the eye, as described in connection with FIG. 2. The trigger switch 397 is mounted to the housing 502 as illustrated in FIG. 5A. The switch 397 performs the functions as described in connection with FIG. 3. In particular, when a user is ready for the apparatus 500 to perform a measurement, the user presses the trigger switch 397. After the trigger switch is pressed, successive wavefront measurements are obtained by the wavefront sensor 116 illustrated in FIG. 2, and the determination and control module 220 adjusts the visual tunable lens 110 to simulate eyeglass correction.

Each time the visual tunable lens 110 is adjusted, the light source tunable lens 210 can be adjusted by a compensating amount to cause the eye illumination light 240 to form a focused spot 207 at the retina of the eye 106. These adjustments can be performed iteratively, as further illustrated hereinafter in connection with FIG. 6, until the user is satisfied with the simulated refractive correction. Once the user is satisfied, the user can again press the trigger switch 397 to indicate that the correction is satisfactory. In other embodiments, the user or a technician or other person assisting can press and hold a trigger switch while iterative adjustments are performed, and release of the trigger switch can indicate that a user is satisfied with the correction.

The apparatus 500 also includes reporting screen 554 that is configured to display a lens prescription intended for the patient (user). In various embodiments, the reporting screen 554 can be configured to display a contact lens prescription, a wavefront spot pattern for alignment or other purposes, or other information described in connection with the reporting interface screen 354 illustrated in FIG. 3, for example.

FIG. 5A also shows a lensometer attachment 591, modularly attached to the apparatus 500 via a modular interface 592, for performing lensometer measurements for eyeglasses 598. The housing 502 is thus configured to receive a lensometer attachment 591 that is configured to receive and support a corrective lens intended to be worn by a person. The lensometer attachment 591 can also be configured to support a lens blank that is intended to be manufactured into a corrective lens; in this way, the lensometer attachment 591 is useful for both lensometer measurements in a clinical setting and for analysis of lenses and lens blanks during a lens manufacturing process. The wavefront sensor can measure the wavefront of the light received through the corrective lens or lens blank. A determination module, such as module 120 in FIG. 1 or module 220 in FIG. 2, can be configured to determine a refractive property of the corrective lens or lens blank based on a lens wavefront of light received through the corrective lens or lens blank.

In FIG. 5A, the lensometer attachment 591 includes lens holding bays 594 for placement of the pair of eyeglasses 598, with each lens in its own isolated bay. A calibration reservoir 595 including artificial eyes (model eyes) 599 is also included in the attachment 591 for aligning two optical components of known optical wavefront properties to two respective optical channels in the apparatus 500. The calibration reservoir 595 may also be referred to as calibration holder or calibration bay.

The attachment 591 in FIG. 5A also includes a sliding track and mechanism 596 between the modular interface 592 and the calibration reservoir 595 to clamp the optical components of the eyeglasses 598 in a manner to minimize movement and stabilize the eyeglasses for lensometer measurements. The sliding track and mechanism 596 can be used to set a distance between the two channels of the binocular apparatus 500. When the apparatus 500 is used to determine a refractive correction for someone's eye, the sliding track and mechanism 596 can be used to adjust the binocular apparatus 500 to match the interpupillary distance (i.e., the distance between the eyes of the user). When the apparatus 500 is used for lensometry on a pair of eyeglasses, then the sliding track and mechanism 596 can be used to match the binocular apparatus 500 to a distance between respective optical centers of the two lenses of the eyeglasses. The trigger switch 397 also causes the apparatus 500 to trigger a lensometer measurement through the initiation of a software calibration sequence.

The artificial eyes 599 are shown included in the calibration reservoir 595 for calibration purposes. The artificial eyes 599 can act as known aberrations so that aberrations due to the eyeglasses can be determined. The lensometer attachment 591 can be similar in some of its internal structure to a calibration cradle 517 described further hereinafter in connection with FIGS. 5D-5K. In particular, there can be reservoirs in which to hold the artificial eyes and slots in which eyeglass lenses can be placed.

The tunable lens 110, which is used in the apparatus 500 for eye measurement purposes as further described herein, can be optionally used or removed from the apparatus for lensometer purposes. Where the tunable lens 110 is used, it can be held at a fixed optical power so as to shift the measuring range of the apparatus 500 in case the eyeglass lens being measured fall outside the base range of the apparatus.

FIGS. 5B-5C are side-view illustrations of the apparatus 500 illustrated in FIG. 5A. In particular, FIG. 5D shows the eyeglasses 598 outside of the lensometer attachment 591, while FIG. 5C shows the eyeglasses 598 inserted into the lensometer attachment. These side-view illustrations also show that the apparatus 500 includes a second trigger switch 397 at the bottom side of the housing 502.

It will be noted from FIG. 5A that the apparatus 500 is binocular in design. In some binocular embodiments, both sides of the apparatus, addressing opposite eyes of a person using the apparatus, are designed to include optical elements similar to those illustrated in FIG. 2. In this way, measurements can be obtained for both eyes of a person using the apparatus at the same time. Embodiment apparatuses similar to that described in connection with FIGS. 5A-5C can simplify alignment of both eyes simultaneously with respective sides of the apparatus.

However, in the embodiment illustrated in FIGS. 5A-5C, one side of the apparatus 500 is configured to perform wavefront aberrometry measurements of the eye or eyeglass lens placed in front of the port 505, while the other side of the apparatus 500 is configured to have the same light transmission characteristics as the measurement-optical channel, but can otherwise be passive and see-through (i.e., open view). This can ensure that the user has a similar view through both eyes, instead of having the view of one eye brighter than the view of the other eye, for example. Thus, in order to perform both measurements on both eyes using the apparatus 500, the apparatus can be rotated 180° to address opposite eyes of a person using the apparatus 500, and opposite lenses of eyeglasses when used in lensometer mode, each eye or eyeglass in turn. Such open-view, binocular embodiments can permit the viewing conditions of both eyes to be similar to each other. This is in contrast to existing small wavefront aberrometers that are neither open view nor binocular, which makes the viewing conditions of the patient's two eyes different, which can negatively affect binocular subjective refraction (natural viewing).

FIG. 5D is a side-view illustration of the calibration cradle 517, referenced hereinabove, which can be used to calibrate the apparatus 500 illustrated in FIGS. 5A-5C. The calibration cradle is configured to be modularly attached to the housing 502, particularly to the eyecup 504 to obtain a reference wavefront measurement for a perfect eye in the absence of refractive correction from eyeglasses or the aberrations due to a living eye. An artificial eye assembly 519 can be mechanically attached to the calibration cradle 517 to fulfill this purpose.

Figure 5E:
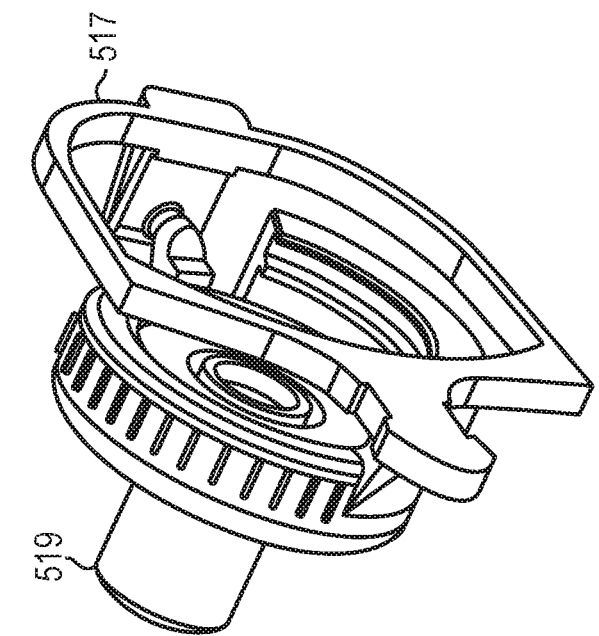
FIG. 5E is a perspective view of the calibration cradle illustrated in FIG. 5D, with the artificial eye assembly attached thereto.
Figure 5D:
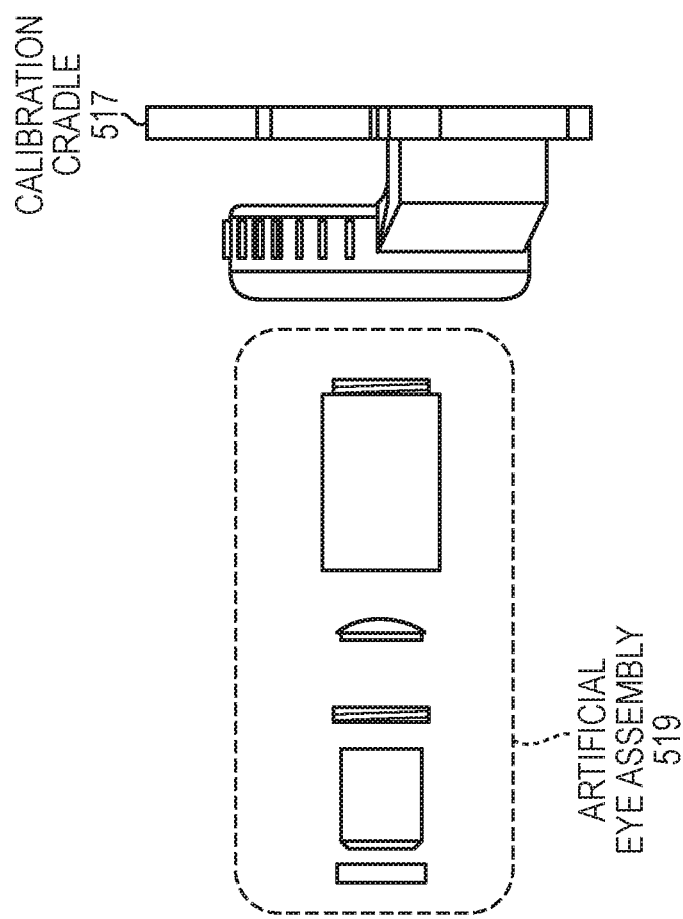
FIG. 5D is an exploded, side-view illustration of a calibration cradle and artificial eye that can be used to calibrate the apparatus illustrated in FIGS. 5A-5C.

FIG. 5E is a perspective view of the calibration cradle 517 with the artificial eye assembly 519 attached thereto.

Figure 5I:
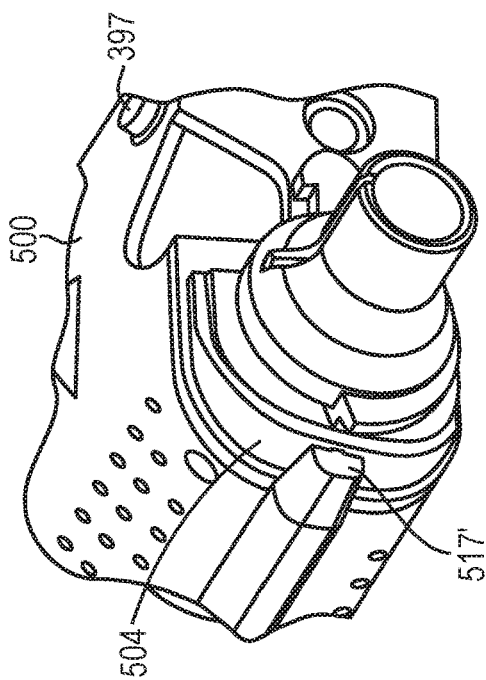
FIGS. 5F-5K are various illustrations of a calibration cradle assembly similar to that shown in FIGS. 5D-5E.
Figure 5K:
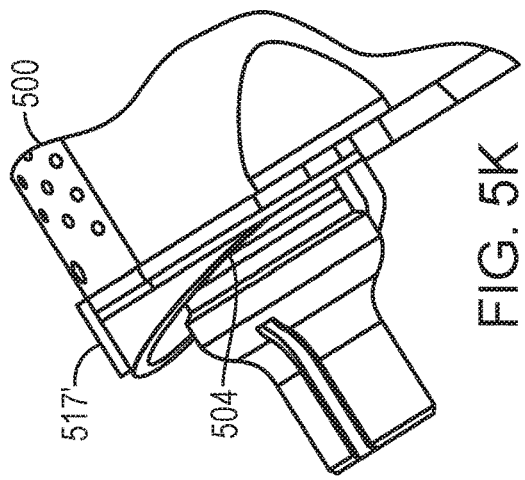
Figure 5G:
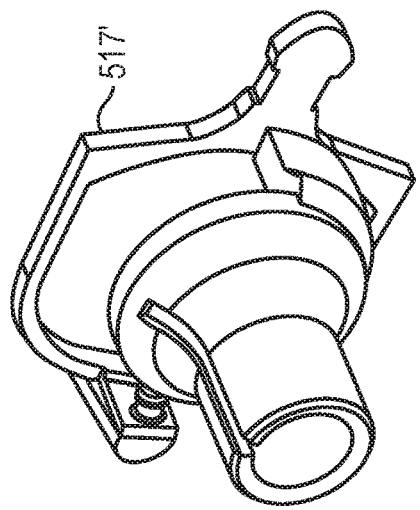
Figure 5J:
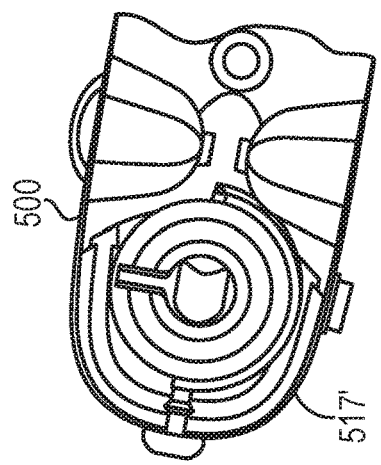
Figure 5F:
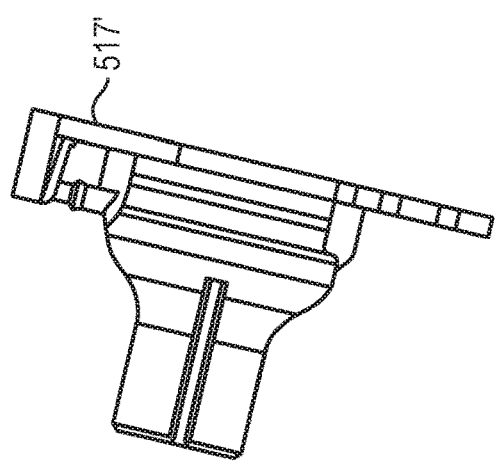
Figure 5H:
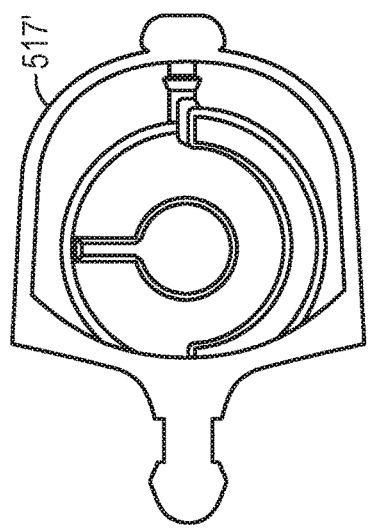

FIGS. 5F-5K are various illustrations of a calibration cradle 517' similar to the calibration cradle 517 illustrated in FIGS. 5E-5F. The calibration cradle 517' is assembled with the artificial eye assembly 519. In particular, FIG. 5F is a side-view illustration of the assembly, FIG. 5G is a perspective view of the assembly, and FIG. 5H is an end-view illustration of the cradle 519. FIGS. 5I, 5J and 5K are various illustrations showing the calibration cradle 517' attached to the apparatus 500.

Using the calibration cradle 517 or 517' attached to the apparatus 500, the apparatus 500 can determine a lens wavefront error due to the visual tunable lens alone for calibration purposes. As is known, tunable lenses can have lower optical quality than fixed lenses. Thus, with a living eye absent, the artificial eye assembly 519 in place with the calibration cradle 517 or 517', and the artificial eye assembly 519 having known optical characteristics, and preferably characteristics as close as possible to those of a perfect eye, resulting in no wavefront error to the assembly 519, any wavefront error that is measured is principally due to the visual tunable lens 110.

This contribution of wavefront error due to the visual tunable lens can be taken into account by a processor, such as the determination and control module illustrated in FIG. 2, in determining actual wavefront error due to the eye 106. In this way, the optical quality of the visual tunable lens 110 becomes much less important, enabling the device to provide highly accurate measurements and prescription determinations even given the presence of the visual tunable lens 110. Thus, even with a visual tunable lens that has lower optical quality than a fixed lens, the processor may determine the actual wavefront error of the eye 106 with high precision by taking into account precise contribution of the visual tunable lens to wavefront error by calibration.

Figure 6:
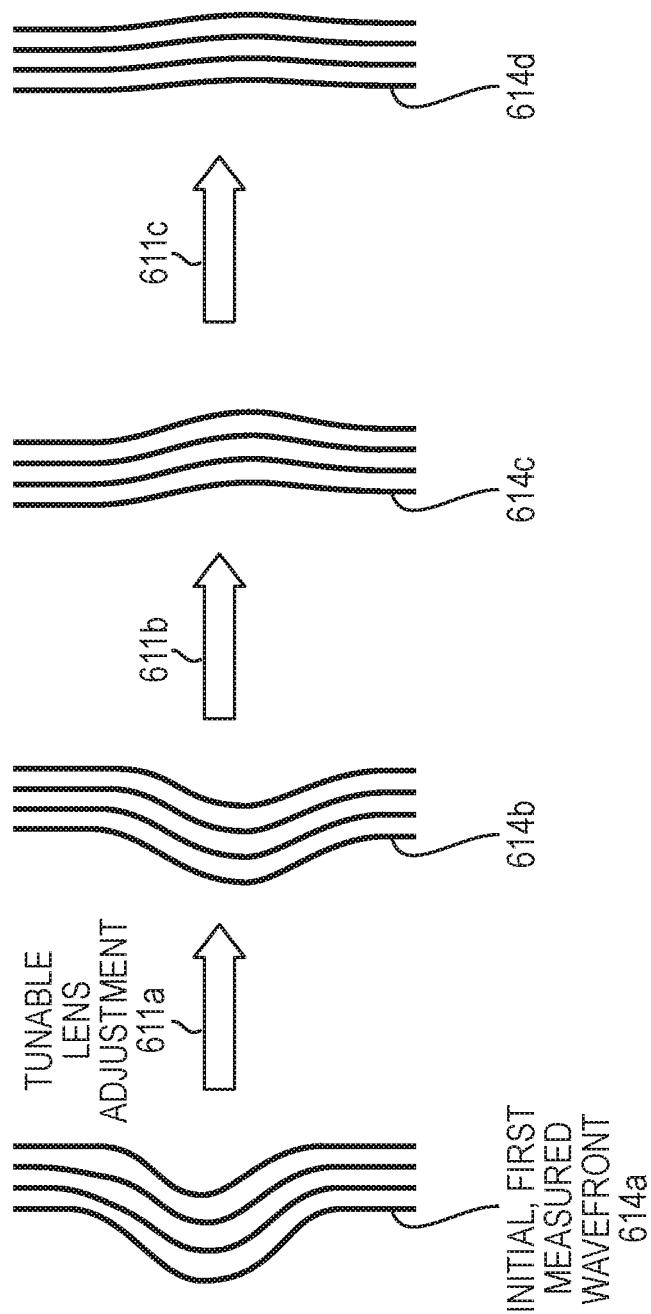
FIG. 6 is a schematic flow diagram illustrating an embodiment iterative process for minimizing wavefront errors due to aberrations of an eye using the visual tunable lens illustrated in FIGS. 1-2 and for simulating the effects of eyeglasses.

FIG. 6 is a schematic flow diagram illustrating an iterative process for correcting wavefront errors due to aberrations of an eye using the visual tunable lens illustrated in FIGS. 1 and 2 and for simulating the effects of eyeglasses. Furthermore, where a light source tunable lens is used, as in FIG. 2, compensating adjustments may be made as follows.

A wavefront 614a is initially measured by the wavefront sensor 116 in FIG. 2, with no optical power applied by the visual tunable lens 110. An arrow 611a represents a tunable lens adjustment applied to the visual tunable lens 110 illustrated in FIG. 2. At this point, a corresponding, compensating adjustment can be made to the optical power of the light source tunable lens 210 illustrated in FIG. 2 in order to compensate for the effect of the visual tunable lens 110 adjustment on the eye illumination light and to maintain the eye illumination light focused onto a spot on the retina. A wavefront 614b is then measured by the wavefront sensor 116, which exhibits less wavefront error (less deviation from ideal planar wavefront).

Subsequently, an arrow 611b illustrates application of further adjustment to the visual tunable lens 110 to apply a more minor adjustment to simulate a better eyeglass correction, with corresponding adjustment made to the light source tunable lens 210. A wavefront 614c is then measured by the wavefront sensors 116. In this case, it can be seen that the wavefront 614c exhibits some over-correction having been applied by the visual tunable lens. An arrow 611c represents further minor adjustment to the visual tunable lens 110 to simulate eyeglass correction, as the simulation can best be applied using the parameters available with a specific visual tunable lens. As previously described, these adjustable parameters can include sphere, cylinder, and axis for particular tunable lenses. In addition, as tunable lenses continue to be developed and improved, it is expected that particular tunable lenses will be able to adjust and correct for higher-order corrections as well. In the case of higher-order corrections, similar iterative adjustments can be performed. A further, minor, compensating adjustment can be made to the light source tunable lens 20.

A final wavefront 614d is measured by the wavefront sensor 116, representing the best wavefront that can be obtained using the particular visual tunable lens 110, in view of any optical aberrations present in the visual tunable lens and in other optical components of the system. The schematic flow diagram illustrated in FIG. 6 can include many more iterations, depending on eye alignment stability, eye accommodation, reproducibility of wavefront measurements, potential averaging of subsequent wavefront measurements to obtain best estimates, etc. At each successive wavefront error measurement, a minimum (or maximum) error in wavefront may be determined. One way to characterize wavefront error is by means of a root mean square (rms) wavefront measurement, for example. However, other measures of wavefront error may also be used.

Furthermore, the iterative adjustment and measurement process illustrated in FIG. 6 can be applied to multiple parameters of the visual tunable lens 110 successively. For example, in example methods, the spherical adjustment of the tunable lens can be optimized with respect to the measured wavefront followed by subsequent optimizations of cylinder and axis, for example. This process can then be repeated (sphere, cylinder, and axis measured again) for further optimization. Because of the potential speed of adjusting tunable lenses, as described hereinabove, for updating lens settings, together with the acquisition speed for wavefront sensing (e.g., ten frames per second), this process can proceed very quickly, even when multi-dimensional and iterative.

Figure 7:
FIG. 7 is a flow diagram illustrating an embodiment procedure for determining a property of an eye.

FIG. 7 is a flow diagram illustrating a procedure 700 for determining a property of an eye. The property can include wavefront error produced by the eye, a refractive prescription for the eye, an accommodation range measurement, a presbyopia measurement, a phoropter measurement, and other measurements as described herein. Embodiment devices described herein, such as those described in connection with FIGS. 1-5K, may be used to perform the example procedure 700.

At 713a, a variable focal power is applied to light received from an eye, via a port of a housing configured to receive the eye, using a visual tunable lens. At 713b, light is passed from the eye along an optical path. At 713c, a wavefront of the light from the eye is measured, with the light being received via an optical path from the port of the housing.

At 713d, a property of the eye is determined based on the wavefront of the light from the eye. Further details regarding embodiment procedures encompassed by procedure 700 are described hereinafter.

Figure 8A:
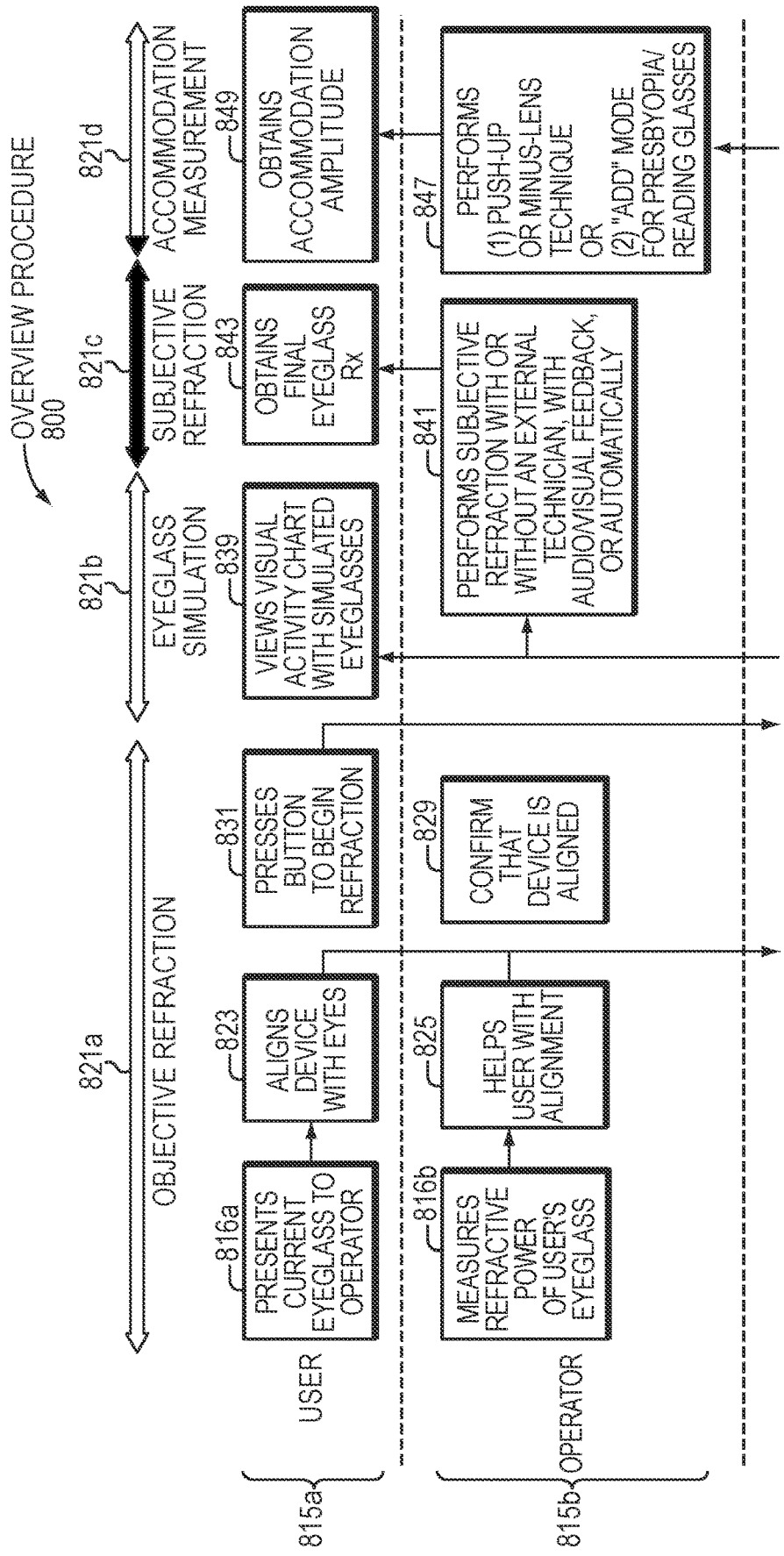
FIGS. 8A-8B are an overall flow diagram illustrating various measurement procedures that can be performed using embodiment devices such as the "QuickSee" apparatus illustrated in FIGS. 5A-5C.
Figure 8B:
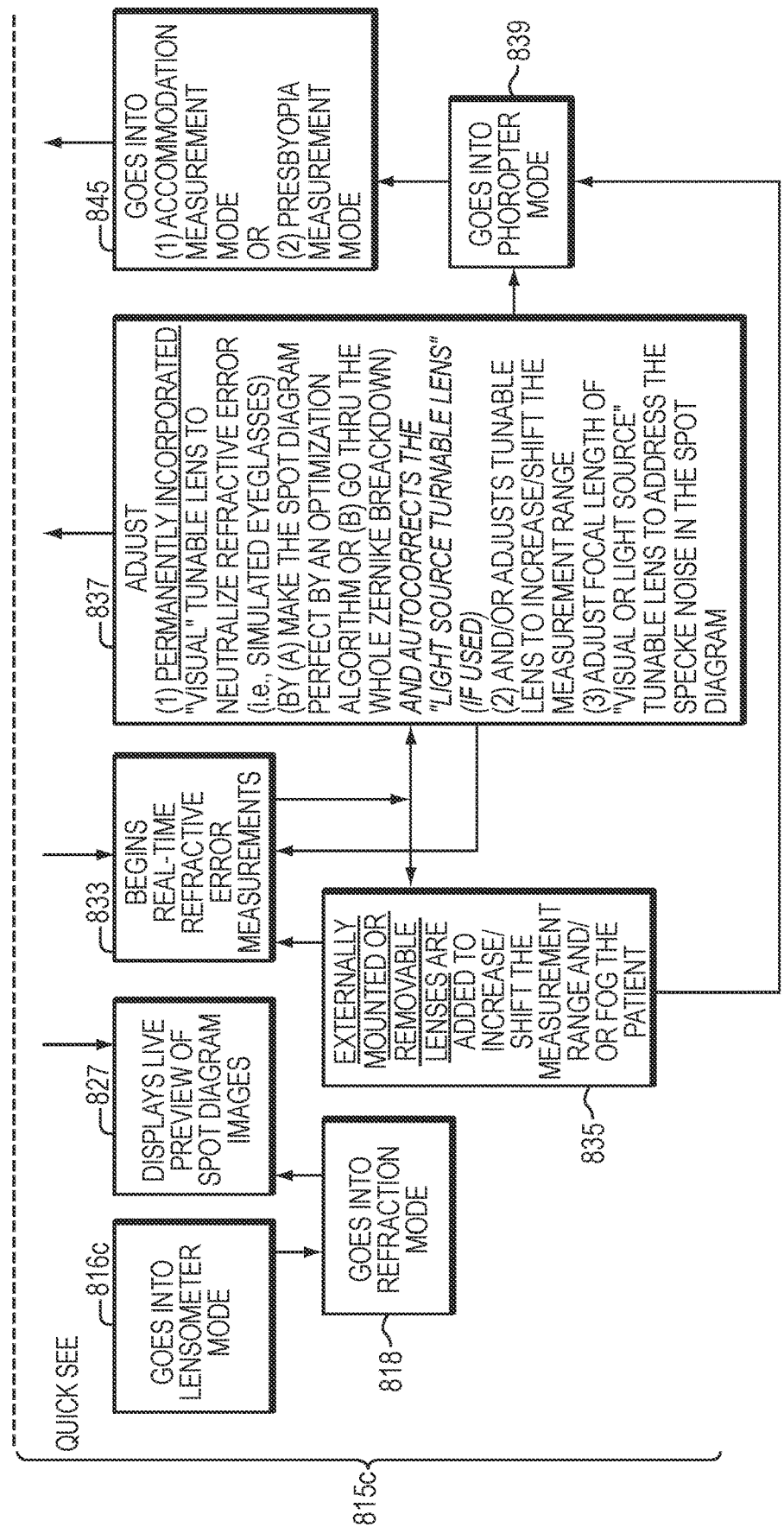

FIGS. 8A-8B are a flow diagram illustrating an overview procedure 800 including various measurements that can be performed on an eye patient, as well as an example clinical examination flow, using the embodiment apparatus illustrated in FIGS. 5A-5C. Because the embodiment apparatus in FIGS. 5A-5C (also referred to herein as the "QuickSee" apparatus) can include various features similar to those illustrated in FIGS. 1-4, reference is also made to those figures.

Row 815a in FIG. 8A indicates operations that can be performed by a user, such as a person whose eyes are being measured using the QuickSee apparatus. Row 815b shows operations that can be performed by an operator, such as a technician, for example. In other embodiments, the actions described in row 815b can be performed by the user or can be performed automatically using an embodiment apparatus. Furthermore, other operations can be performed using embodiment devices by the user, an operator, or an optometrist or ophthalmologist, for example. Row 815c shows example actions that can be performed by the QuickSee apparatus.

Column 821a in FIGS. 8A-8B illustrates operations that can be used to identify an objective refractive correction. An objective refractive correction, as used herein, denotes a measurement that can be performed without regard to subjective refractive preferences of the user. For example, a refractive correction can be objectively estimated using embodiment devices based on the wavefront representation 118 obtained by the wavefront sensor 116 illustrated in FIG. 2, for example. Column 821b illustrates operations that can be used to improve an objective correction estimate by simulating the effect of refractive correction of eyeglasses by using a tunable lens, such as the visual tunable lens 110 illustrated in FIG. 2, for example.

Column 821c in FIGS. 8A-8B illustrates subjective refraction operations that can be performed to improve objective refraction estimates by obtaining feedback from a user regarding lens preferences, for example. This process is normally referred to as phoroptry when performed using a standard phoropter having a variety of fixed lenses in the clinic of an optometrist, for example. However, advantageously, in accordance with embodiments described herein, phoroptry can be performed using embodiment devices automatically or semiautomatically by taking advantage of tunable lenses. Column 821d illustrates example operations that can be performed using embodiment apparatus and methods to obtain eye accommodation range measurements.

In accordance with the objective refraction process described above, at 816a, the user optionally presents existing eyeglasses to an operator (e.g., technician). At 816b, the operator measures refractive power of the user's existing eyeglasses using the lensometer attachment 591 further described in connection with FIGS. 5A-5C. In order to perform lensometry, at 816c, the QuickSee apparatus goes into lensometry mode. Following lensometry, at 818, the lensometer attachment 591 is removed, and apparatus 500 goes into refraction mode for objective measurement of at least one of the user's eyes.

One advantage of using a visual tunable lens for lensometry includes the fact that a measuring range can be easily shifted by implementing a fixed tunable lens offset, for example. This is useful in case a particular eyeglass lens being measured is outside the base range of the apparatus. A further advantage of using a visual tunable lens for lensometry involves measurement accuracy. In particular, similar to the accuracy advantage described hereinabove for eye wavefront measurements in the presence of a visual tunable lens, lensometry accuracy can be improved by setting the visual tunable lens to negate the optical power of the eyeglass lens being measured so that the detected wavefront is as parallel as possible. As further described hereinabove, when the detected wavefront is as parallel as possible, then the wavefront measurements themselves can be more accurate, thus leading to more accurate lensometry when based on wavefront measurements. In this case, the measured optical power of the eyeglass lens can be determined based on the combination of the measured wavefront and the optical power implemented At 823, a user having the eye to be measured aligns an embodiment apparatus with an eye or eyes to be measured. The user puts the device in contact with the user's face and looks through the apparatus at a distant target. The user keeps the user's eyes open, with occasional blinking. At 825, the operator helps the user with the alignment process. In some embodiment procedures, alignment instructions are provided by the apparatus, such as through the speaker 362 illustrated in FIG. 3. At 827, as part of the alignment process, the QuickSee apparatus displays a live preview of spot diagram images provided by the wavefront sensor 116. These images can be shown at a reporting interface screen, such as that illustrated in FIG. 3, or at a screen of an attached cellular phone, as described in connection with FIG. 4, for example.

At 829, the operator confirms that the QuickSee apparatus is aligned with the eye of the user. In other embodiments, this can be performed automatically, using feedback from the device itself. Whether alignment is confirmed manually by the operator or automatic alignment feedback is provided, alignment analysis can be based on the spot diagram from the wavefront sensor. As the user looks through the apparatus, the degree to which the user's eye is optically centered with the wavefront sensor can be analyzed. In particular, this can be done by checking how well the spot diagram is centered on the wavefront image sensor and then providing feedback on how to move the device relative to the user's face in order to optically center the user's eye to the wavefront sensor.

At 831, the user can press the trigger switch 397 illustrated in FIG. 5A to indicate that refractive measurements should begin. Following this, at 833, the QuickSee apparatus begins real-time refractive error measurements. Then, at 835, as necessary, externally mounted or removable lenses can be added as modular attachments to the QuickSee apparatus to shift a measurement range of the visual tunable lens or to fog the patient's view. The addition of these lenses may be performed by the operator, for example. As described hereinabove, the example Varioptic Visayan® 80S0 tunable lens can apply variable focus optical power between −12 and +12 dpt. Therefore, if this lens is used as the visual tunable lens, and the patient's eye has a spherical error of about −12 dpt, for example, then the tunable lens may not provide a convenient range of adjustment to ensure that optimum refractive correction is determined and simulated for the patient. In this example case, an additional, externally mounted, +5 dpt fixed lens could be added to the apparatus and used to shift the measurement range by +5 dpt for measurement and simulated refractive correction. In alternative embodiments, a different visual tunable lens having a different measurement range could be used.

As described hereinabove in connection with FIG. 2, for example, the eyepiece proximal port 205 can be configured to accept one or more additional, modular, fixed lenses as needed. As an alternative, a user may be given instructions by the QuickSee apparatus, through the reporting interface screen 354 or the speaker 362 illustrated in FIG. 3, for example, to insert specific lenses for offset or fogging.

As to the eyeglass simulation column 821b, at 837(1), the permanently incorporated visual tunable lens 110 illustrated in FIG. 2 is adjusted in order to neutralize refractive error caused by imperfections in the eye 106. This process can be iterative as illustrated in FIG. 6, for example. When the refractive error is made as close as possible to zero, indicated by plane waves in FIG. 6, and by a uniform, evenly spaced spot diagram from a Hartmann-Shack wavefront sensor, for example, and the tunable lens 110 is adjusted to achieve such results, then the eye 106 views the external target object 252 through the open view apparatus 200. Then, the eye 106 is effectively viewing through a corrective lens simulated by the visual tunable lens 110. This neutralization process can be completed empirically by running an optimization routine to make the spot pattern on the wavefront sensor as uniform as possible. An example optimization procedure is described hereinafter.

The optimization procedure to make the spot pattern as uniform as possible can be performed in several ways. One straightforward method is to minimize the root mean squared (rms) error of the wavefront with respect to an aberration-free wavefront. Examples of other well-known parameters which may be used in the optimization procedure are the peak-to-valley (P-V) wavefront aberration or the Strehl ratio, among others. Some of these methods are described in the following paper: "Thibos et al, Accuracy and precision of objective refraction from wavefront aberrations, Journal of Vision 2004 (4), 329-351." The optimization procedure can be performed iteratively using a standard closed loop control in which the feedback signal (error signal) is given by any of the aforementioned parameters.

Another possibility to perform the optimization procedure is to maximize the optical or visual quality. This approach is based on the fact that mathematically is easy to add to the eye's aberration map that our device is continuously measuring. Using the measured spherical and/or cylindrical wavefront (which simulates the correction) we can then compute the resulting retinal image using standard methods of Fourier optics. The curvature of the added wavefront can be systematically or iteratively varied to simulate a through-focus experiment that varies the optical quality of the eye+lens system over a range. Given a suitable metric of optical quality (such as the Strehl ratio), this computational procedure yields the optimum lens needed to maximize optical quality of the corrected eye.

Alternatively, wavefront error optimization can be based on Zernike coefficients. Zernike coefficients can be obtained in each measurement by the determination and control module 220 and can be used to calculate the RMS error of the wavefront obtained by the wavefront sensor 116 (or any other parameter of interest). This parameter can be used as error signal in a closed loop to adjust the Sphere, Cylinder and Axis in the visual tunable lens in order to minimize the RMS error. Furthermore, for each measurement, the iterative process may be performed to calculate the adjustments to apply to the visual tunable lens 110 based on optical or visual quality metrics obtained after retinal image quality estimation.

As a further alternative, the determination and control module 220 may calculate Zernike coefficients based on the wavefront obtained by the wavefront sensor 116, and spherical, cylinder, and axis adjustments to the visual tunable lens 110 may be made to compensate for corresponding refractive error components indicated by the Zernike expansion. One simple example method includes causing the tunable lens 110 to correct for second order Zernike terms (defocus, oblique astigmatism, and vertical astigmatism).

During this process, in each case of adjustment of the visual tunable lens 110, the light source tunable lens 210 can be adjusted by a corresponding amount to maintain a focused spot of the illumination light 240 on the retina.

At 837(2), the visual tunable lens 110 can be adjusted to increase or shift the measurement range. The correction objectively determined based on wavefront measurements can be implemented as a fixed value for eyeglass simulation. Further, this simulation can be implemented as a coarse offset, and then, in the subjective refraction stage, be allowed to vary over a relatively small range, such as +/−1.0 dpt, +/−0.5 dpt, or +/−0.25 dpt, for example, based a user's preferences. At 837(3), during the real-time measurement and iterative neutralization process described above, the visual tunable lens 110 or the light source tunable lens 210 may be adjusted slightly (dithered) to address speckle noise in spot diagrams obtained by the wavefront sensor 116. This process is further described hereinabove in connection with FIG. 2.

At 839, with the spot diagram detected by the wavefront sensor 116 optimized to be uniform and to indicate minimized refractive error by adjustments of the visual tunable lens 110, the user can view a standard visual acuity chart, through the open view apparatus, with a simulated eyeglass provided by the visual tunable lens 110 through which the user views.

In column 821c, at 841, the visual tunable lens 110 has already been set to an optical power to simulate the best estimate for refractive correction based on objective refraction, using measurements of the wavefront sensor. With this setting as a starting point, subjective refraction is performed, in a manner somewhat similar to phoroptry. However, with the benefit of the visual tunable lens 110, this process can be performed automatically or semi-automatically, with minimal help from an external technician, or by the user alone, all while the user views through the same apparatus used for wavefront aberrometry and objective refraction.

In one embodiment, the speaker 362 provides an audible message to the user to turn the dial 356. While still viewing the visual acuity chart (e.g., Snellen chart, Log MAR chart, EDTRS chart, or tumbling E chart) or another target, the user adjusts the dial 356 to optimize the view for the eye under test, and sphere is adjusted for the visual tunable lens 110 in accordance with the dial 356 adjustments. Subsequently, the speaker 362 asks if the view is optimized. The user responds, through the microphone 364, "yes." Then, the speaker 362 provides a message to again optimize the view using the dial 356. This time, the cylinder adjustment of the visual tunable lens 110 is made with the user still viewing the visual acuity chart. After similar adjustments of the dial and a similar confirmation through the speaker and microphone, an axis adjustment can be made similarly. After this process, it may be desirable to iterate, by once again asking the user to adjust the dial 356 to optimize sphere, and so forth.

In another embodiment, the user uses the directional buttons 358 to adjust sphere correction up or down, as desired. In another embodiment, an external technician provides assistance during the subjective refractive measurement. For example, the technician can ask the patient whether the patient sees more clearly with a first tunable lens setting or a second tunable lens setting, and so on, thus guiding the patient through an entire subjective measurement process. The technician can perform subjective refraction using the QuickSee apparatus as, essentially, a phoropter. Switching of visual tunable lens settings may be done by direct input to the device. However, more preferably, input can be via a remote device, such as a tablet computer linked to the QuickSee apparatus. In this case, a tablet computer can be operatively connected to the QuickSee apparatus much like the cellular phone 492 illustrated in FIG. 4, for example. In yet another embodiment, the visual tunable lens 110 is slowly varied over a limited range, and the user presses a trigger button similar to the trigger switch 397 when the user's view is optimized with respect to sphere, cylinder, or axis, for example.

At 843, a final eyeglass prescription is obtained based on the final refractive values obtained from subjective refraction. In some embodiments, data are collected, either by the apparatus 200 itself within the determination and control module 220, or by an external monitoring computer connected via the network interface 468 illustrated in FIG. 4. Data regarding the subjective refraction final values, as compared with the objective refraction values, can be accumulated to produce statistics for better prediction of final prescription values.

As described hereinabove, one unique feature of embodiment devices is the ability to perform both objective and subjective refraction using the same device. For each patient whose eyes are measured, embodiment apparatus and methods can be used to obtain (i) an initial objective refraction, and (ii) a final subjective refraction. For each patient, these two values can be logged to see how different they are.

By accumulating and learning from such data, methods can be implemented to effectively modify the objective measurement initially measured to provide a more accurate starting point for subjective refraction. A machine learning approach can take into account not only objective and subjective refractions measured for each patient, but also any user's (eye patient's) personal information (e.g., age, gender, race), or additional information (e.g., high-order aberrations measured objectively, or retinal image quality calculated from the measurements), to be stored and analyzed according to a machine learning method to further improve prediction accuracy.

A useful advantage of embodiments that use this machine learning/prediction approach is that overall time for an entire refraction process can be reduced by having a more accurate starting point for subjective refraction. It is also possible that, given sufficiently developed prediction routines, that subjective refraction need not even be performed, and that prediction of subjective correction may be done solely on the basis of objective refraction results.

As further described herein, the property of the eye measured by an embodiment apparatus can be an objective property based on the wavefront measurements, without taking into account subjective patient preferences that would be reflected in phoroptry results, for example. A determination module can be used to predict a subjective refractive preference of a person having the eye based on the objective property. The determination module can be made to predict the subjective refractive preference based further on a demographic or physical attribute of a patient. Demographic attributes can include age, gender, ethnicity, weight, height, occupation, or another demographic attribute of the patient. Physical attributes can include retinal image quality, axial length, iris color, topography, corneal curvature, aberration of higher order than spherical or cylindrical aberration, or another attribute of the eye, or attribute of a patient's body, which may have some correlation with difference between objective and subjective eye refraction results.

The determination module can be configured to predict the subjective refractive preference using a correlation developed from a database including respective demographic or physical attributes and respective objective eye properties for many different eye patients. A database storing the respective attributes can be included in the memory 470 illustrated in FIG. 4, or in an external server accesses via the network interface 468 in FIG. 4, for example.

In one example, objective and subjective refraction results along with respective ages for many patients examined using an embodiment apparatus can be stored in memory in the apparatus. A determination and control module in the apparatus can determine that the difference between objective and subjective refraction results for the apparatus varies approximately linearly with age of the patient, for example. Then, based on this linear correlation, the determination and control module can predict subjective refraction for a given patient of given age based on the given patient's objective refraction results and the patient's age.

In another example a determination and control module may determine that the difference between objective and subjective refraction results for the apparatus diminishes with the magnitude of the objective refraction results themselves roughly according to a quadratic function. Thus, for a given patient, based on the patient's objective refraction results and the quadratic function, the determination and control module may predict the given patient's subjective refractive preference. The visual tunable lens can then be set to the predicted subjective preference, and further subjective examination may optionally be performed.

It should also be noted that such predictive methods can also be applied to data obtained from devices that only perform objective refraction. Objective results from a wavefront aberrometer, for example, may be compared with subjective phoroptry results over a large sample of patients to develop predictive correlations that can be applied to obtain (effectively) subjective-quality refractive corrections on the basis of objective measurements alone. Nevertheless, it is preferable to develop the correlation between objective and subjective refraction, and the prediction of subjective refractive preference, on the basis of objective and subjective measurements acquired using the same apparatus within the same examination session. Use of the same apparatus in this context can potentially be faster and more consistent.

The determination module 120 in FIG. 1 or the determination and control module 220 in FIG. 2, or another processor that is part of, or separate from, the apparatus in FIGS. 1-2, for example, can perform calculations to predict a subjective refractive preference of a person having the eye based on the property of the eye based on the wavefront. This can be done by comparing, over time, the difference between refractive preferences (phoroptic-type determinations) and objective refraction values as a function of various patient attributes, such as the demographic and physical attributes described hereinabove. Various methods and calculation routines can depend upon the empirical data collected over time. Methods may be used that take into account age, gender, the absolute objective refraction value for the eye, or any other value for the user that may have a correlation with the difference between objective and subjective refractive values. In this way, prediction of subjective refraction, even based on objective refraction alone, may be improved over time.

Column 821*d* illustrates an example procedure for obtaining accommodation amplitude (range) measurements based on patient feedback. At 845, the apparatus 200 goes into accommodation measurement mode (presbyopia measurement mode). At 847, push-up or minus-lens technique is used or "add" mode is used to determine a prescription for reading glasses to deal with presbyopia. At 849, a final accommodation amplitude is obtained.

In order to measure accommodation amplitude (either with push-up or minus-lens technique), it can be assumed that the person who is being tested is emmetropic (i.e. requires no corrective lenses for distance vision) or is properly corrected for distance vision (for example, with eyeglasses or contact lenses). Embodiment devices such as the QuickSee apparatus can provide proper correction for distance vision via a visual tunable lens, which can take the place of a phoropter or set of trial lenses.

The visual tunable lens can be especially advantageous when using the minus lens method to measure accommodation. Traditionally, for the minus lens method, the accommodative demand of a small nearpoint target is changed as minus lenses are introduced to the patient monocularly until the target is no longer clear, based on patient feedback. However, with a visual tunable lens-based apparatus according to embodiments, no additional lenses need to be carried around, and the introduction of more minus power can be done continuously, instead of in a step-wise fashion as done traditionally. The capability for continuously variable power is expected to result in a more accurate measurement of accommodation amplitude.

The procedure illustrated in column 821*d* using embodiment methods and apparatuses differs significantly from existing methods for accommodation measurement. Existing methods typically include using a physical moving target attached to a phoropter. The physical moving target starts a distance away from the person (to correct for distance vision) and is gradually moved towards the patient's eye to track the patient's myopia. At a sufficiently small distance between the eye and movable target (closer than the near point), the eye can no longer accommodate. Existing systems using a moving target can have disadvantages of being physically large, requiring moving parts, requiring actuators for the movement, lacking the ability to cycle between settings quickly, potentially having drift or hysteresis, and causing the eye to over- or under-accommodate if the physical target is moving during measurement and the movement is perceived by the eye or eyes under test. In contrast to existing systems, embodiments described herein can take advantage of a tunable lens for fast, repeatable, accurate accommodation measurements without mechanical moving parts.

A further advantage of embodiments described herein, in contrast to existing methods and systems, is that objective accommodation measurements can be obtained by acquiring wavefront measurements at any time during or between changes to the tunable lens settings, all while the patient views the same distant target through the tunable lens whose settings are changed as needed. In this manner, a very precise determination of accommodation can be obtained, which is not possible with existing methods and systems, even where both lens systems and wavefront aberrometers are both used in the same setting but as part of different systems.

In some embodiments, no subjective feedback from the patient is even required for an accommodation measurement, because wavefront measurements are iteratively made while the tunable lens setting is changed until the wavefront measurements indicate that accommodation is no longer occurring. The accommodation amplitude measurement can be completed more rapidly since there is no need to wait for the patient's verbal responses. Patients that are asked to provide subjective feedback during an eye examination, such as an accommodation range examination, are often stressed about their feedback and even question their own final results because they are not sure whether their responses have been "correct." The objectivity that can be provided by an embodiment tunable lens and wavefront aberrometry combined system can eliminate the stress of these patients. The results can be more repeatable because they are not affected by a patient's anxiety regarding "correct" responses and because of the inherent precision of wavefront aberrometry. The accuracy of the measurements using embodiments described herein can also be more reliable because patient communication issues (e.g., with children, elderly patents, patients that do not speak the same language as a clinician, etc.). An example embodiment method for determining accommodation using an embodiment combined tunable lens and wavefront aberrometry apparatus is further described hereinafter in connection with FIG. 9E.

FIGS. 9A-9F supplement the overall refractive examination flow diagram in FIGS. 8A-8B by illustrating in further detail how specific portions of the flow diagram in FIGS. 8A-8B can be carried out.

Figure 9A:
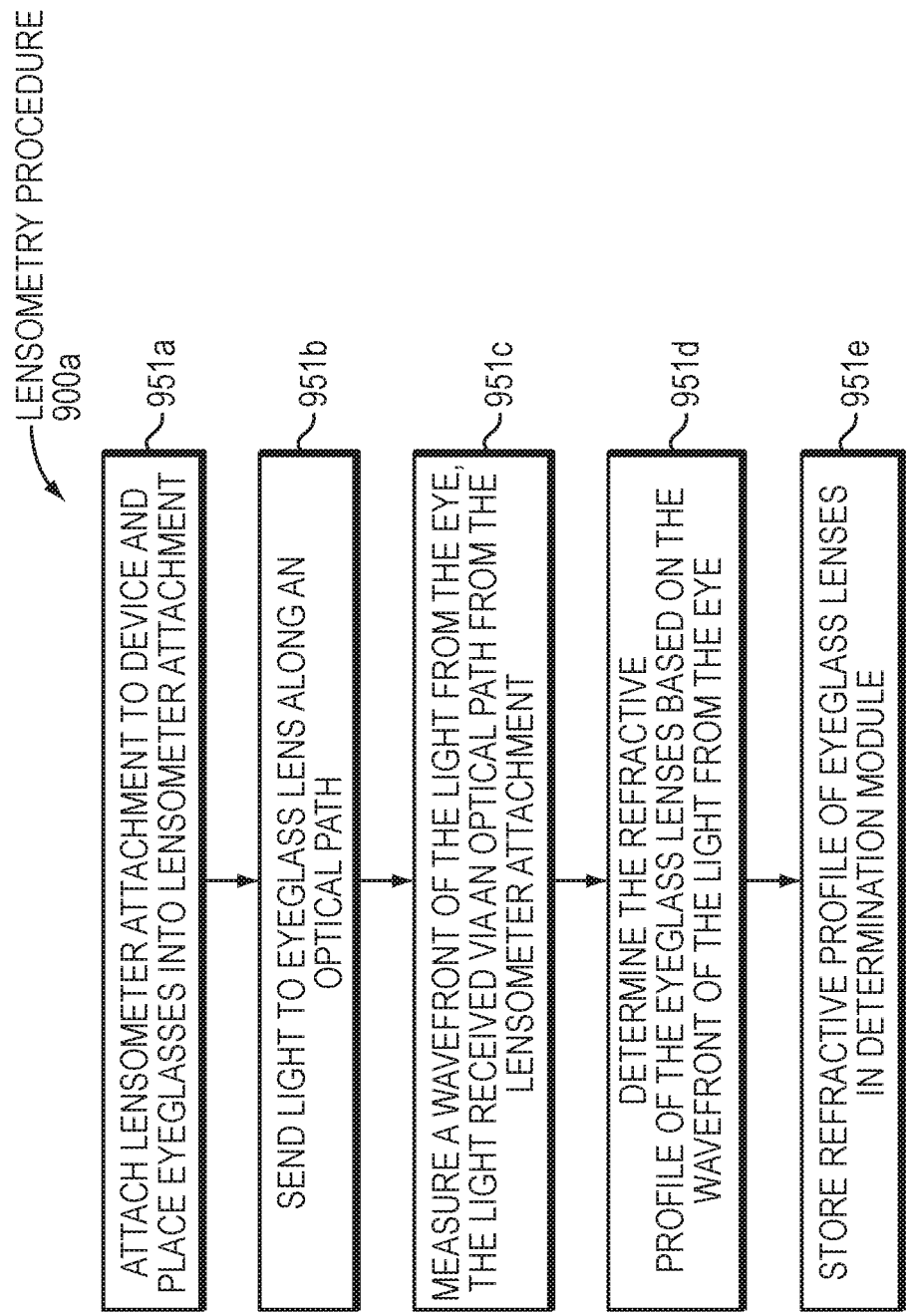
FIG. 9A is a flow diagram illustrating how embodiment devices and methods can be used to perform lensometry.

FIG. 9A shows a procedure 900*a* in flow diagram form illustrating in greater detail how a lensometry measurement may be performed using embodiment apparatuses and methods, as illustrated in summary at element 818 in FIG. 8B. At 951*a*, a lensometry attachment, such as the attachment 591 in FIG. 5A, is attached to an embodiment device. Eyeglasses such as eyeglasses 598 in FIG. 5A are placed into the attachment. At 951*b*, light is sent into the eyeglass lens along an optical path. For example, eye illumination light 240 (illustrated in FIG. 2) can travel along the path illustrated in FIG. 2, exit the apparatus through the tunable lens 110, and enter into the lensometry attachment 591.

At 951*c*, the wavefront of light from the eye, particularly from the artificial eyes 599 illustrated in FIG. 5A, is measured. The light is received via an optical path from the lens on the attachment, similar to the light 108 illustrated in FIG. 2. At 951*d*, the refractive profile of the eyeglass lens is determined by a module, such as the determination and control module 220 illustrated in FIG. 2. At 951*e*, a refractive profile of the eyeglass lens is stored in the determination and control module 220.

Figure 9B:
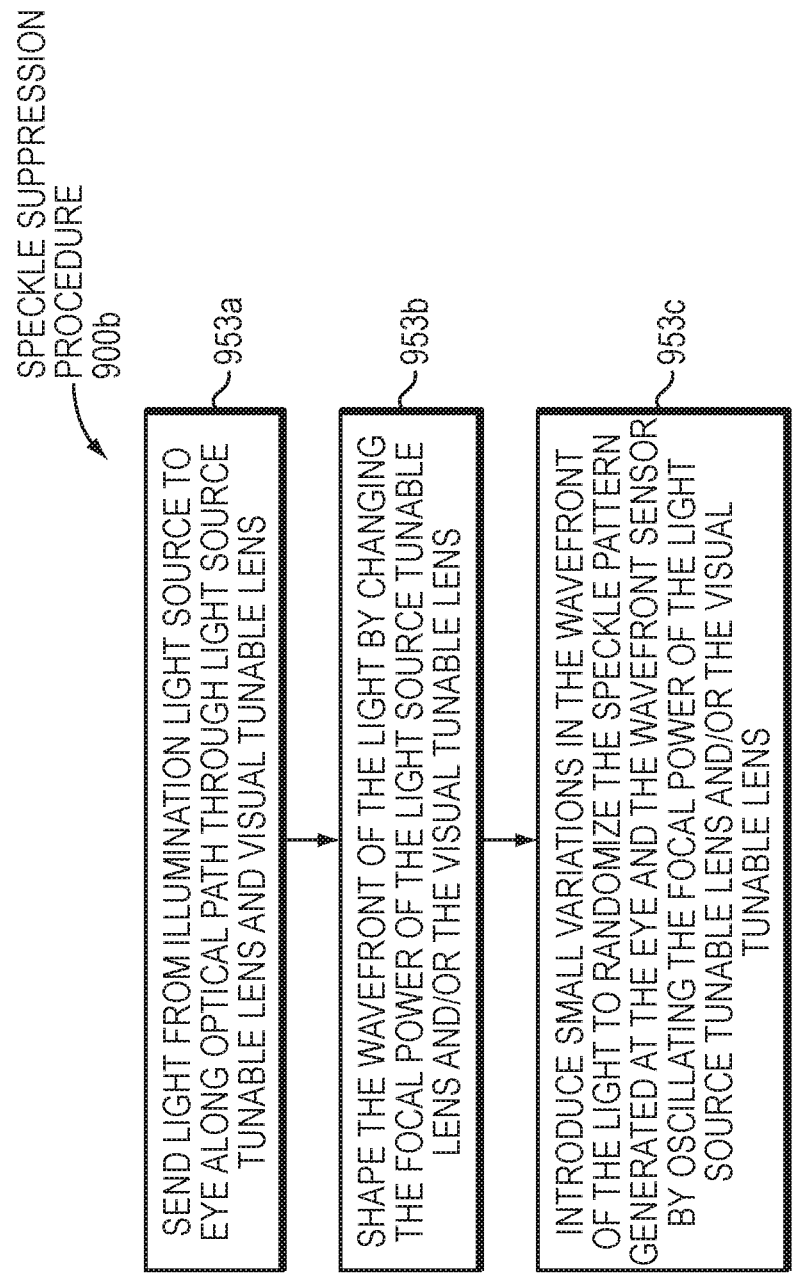
FIG. 9B is a flow diagram illustrating how embodiment apparatus and methods can be used to suppress speckle in wavefront measurements.

FIG. 9B is a flow diagram illustrating in greater detail how speckle in wavefront measurements can be suppressed using embodiment apparatus and methods, particularly by taking advantage of tunable lenses. In a procedure 900*b* illustrated in FIG. 9B, at 953*a*, light is sent from an illumination light source (e.g., source 238 in FIG. 2) along an optical path through a light source tunable lens (e.g., lens 210 in FIG. 2) and through the visual tunable lens (e.g., lens 110 in FIG. 2). At 953*b*, a wavefront of the light is shaped by changing the focal power of the light source tunable lens, or the visual tunable lens, or both. This wavefront shaping can be similar to the iterative shaping illustrated in FIG. 6, for example. At 953c, small variations in the wavefront of the light are introduced, by oscillating the focal power of the light source tunable lens, the visual tunable lens, or both, to randomize the speckle pattern generated at the eye and the wavefront sensor.

Figure 9C:
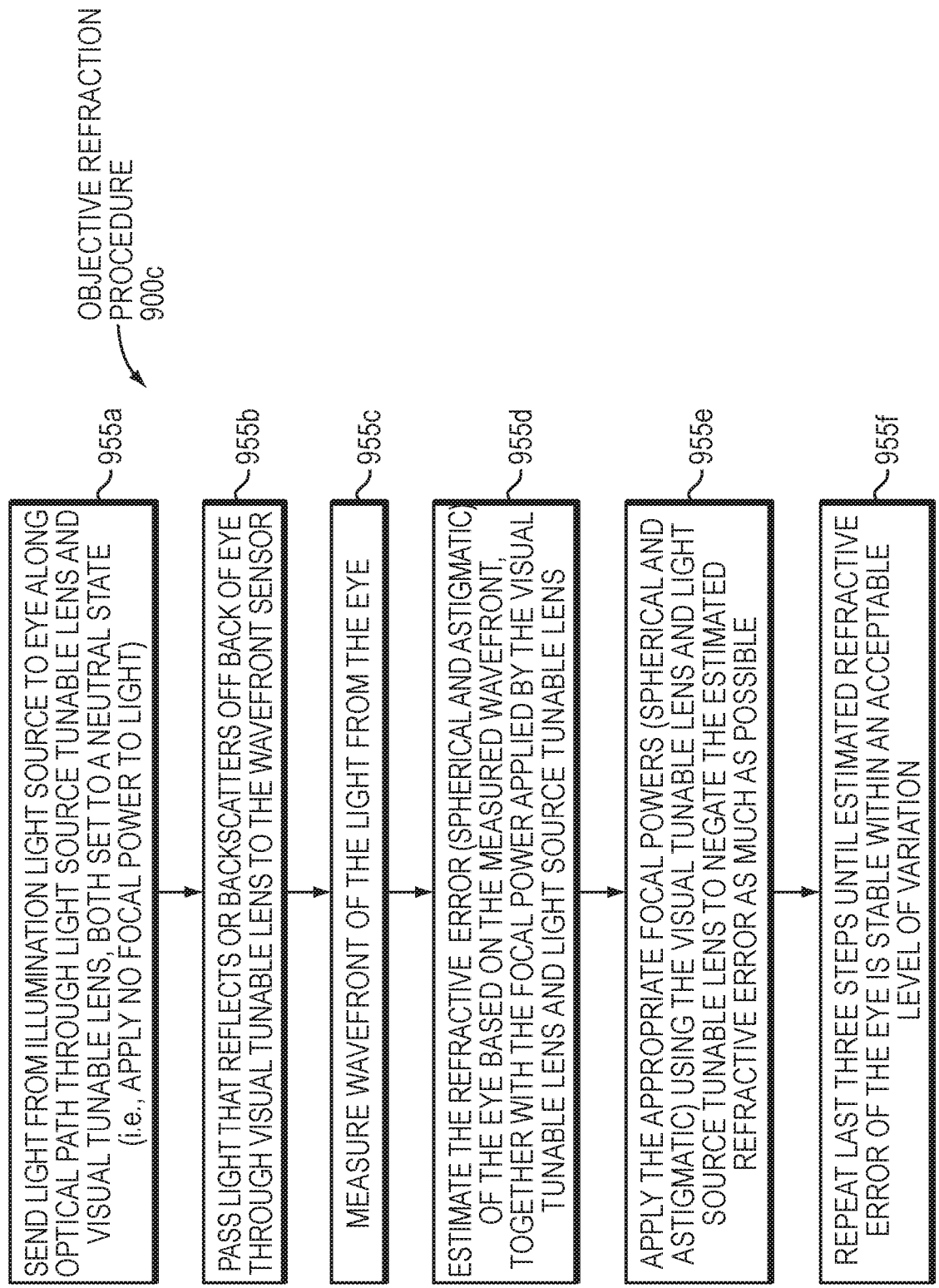
FIG. 9C is a flow diagram illustrating how embodiment devices and methods can be used to perform objective refraction measurements.

FIG. 9C is a flow diagram illustrating in greater detail how objective refractive measurements may be obtained using the embodiment apparatus and methods, particularly by taking advantage of a visual tunable lens according to an objective refraction procedure 900c. At 955a, light is sent from an illumination light source, to an eye, along an optical path through a light source tunable lens and a visual tunable lens. Both the light source tunable lens and visual tunable lens are initially set to apply zero focal power. At 955b, light that is reflected or backscattered from the retina of the eye is passed through the visual tunable lens to a wavefront sensor.

At 955c, a wavefront of the light from the eye is measured. At 955d, the refractive error (e.g., spherical and astigmatic) of the eye is estimated based on the measured wavefront, together with focal power applied subsequently by the visual tunable lens and light source tunable lens, as described hereinabove in connection with FIG. 6, for example. At 955e, appropriate focal powers (e.g. spherical and astigmatic) are applied by the visual tunable lens and light source tunable lens to negate an estimated refractive error of the eye to the greatest degree possible in view of the quality and available adjustments of the tunable lenses. At 955f, elements 955c, 955d, and 955e are repeated until an estimated refractive error of the eye is stable to within an acceptable level of variation (e.g., 0.25 dpt, 0.15 dpt, or 0.05 dpt).

Figure 9D:
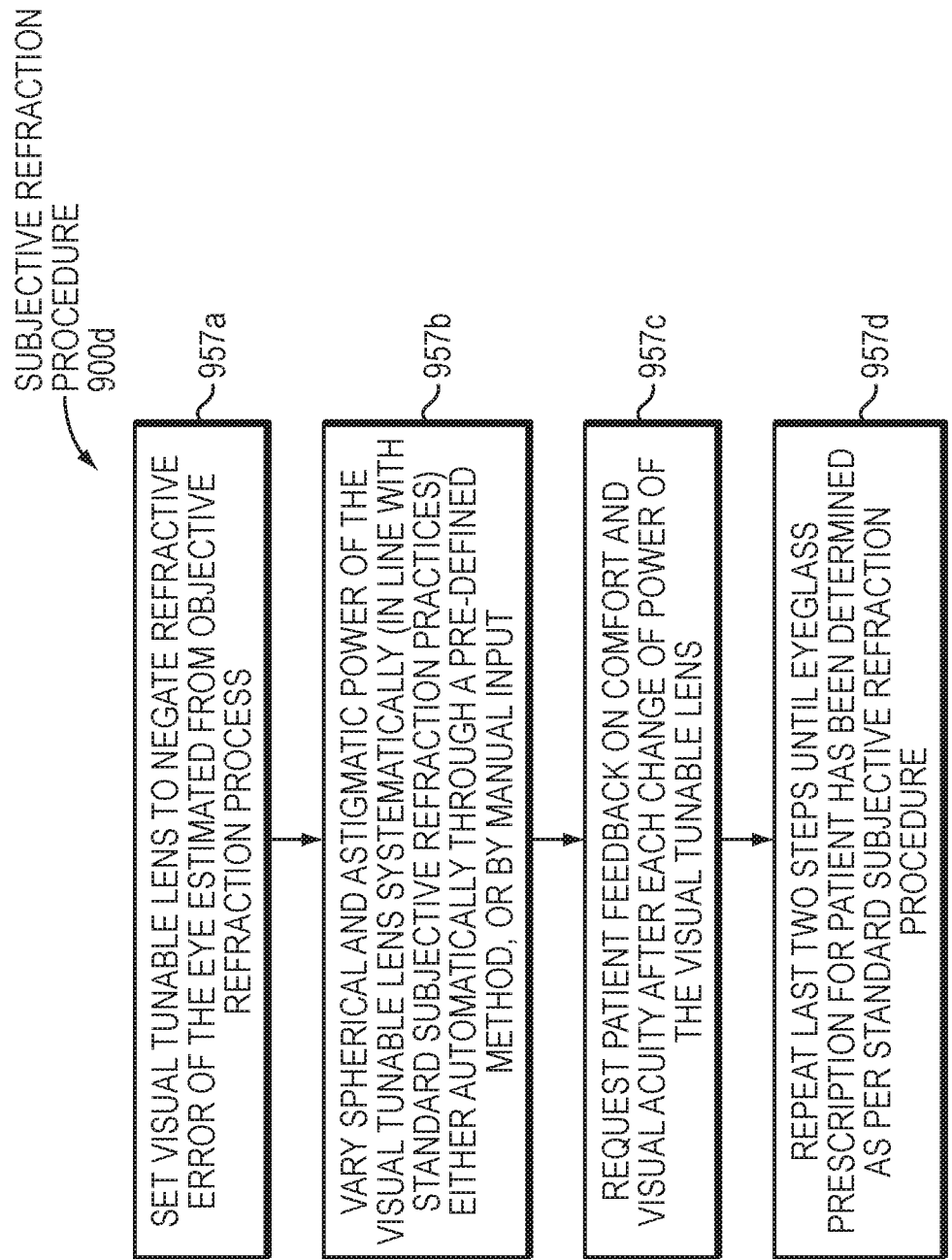
FIG. 9D is a flow diagram illustrating how embodiment devices and methods can be used to perform subjective refractive measurements.

FIG. 9D is a flow diagram illustrating in further detail how subjective refractive measurements can be obtained using embodiment apparatus and methods, according to a subjective refraction procedure 900d. At 957a, a visual tunable lens is set to negate refractive error of the eye of the user, where the refractive error is estimated from an objective refraction process such as that illustrated in FIG. 9C. At 957b, spherical and astigmatic power of the visual tunable lens are varied systematically (in line with standard subjective refraction practices), either automatically through a predefined method, or by manual input from the eye patient or an assistant.

At 957c, eye patient feedback is requested regarding comfort and visual acuity after each change of power of the visual tunable lens. At 957d, elements from 957b-c are repeated until an eyeglass prescription for the eye patient has been fully determined in line with standard subjective refraction procedures (e.g., using a phoropter). Accordingly, because subjective refraction as illustrated in example FIG. 9D may use objective results from example FIG. 9C as a starting point, refractive prescriptions and other properties determined by a determination module such as the module 120 illustrated in FIG. 1 or the determination and control module 220 illustrated in FIG. 2 can be based on both the wavefront aberrometry (objective results) and the tunable-lens-based phoroptry (subjective results) from the same apparatus.

Figure 9E:
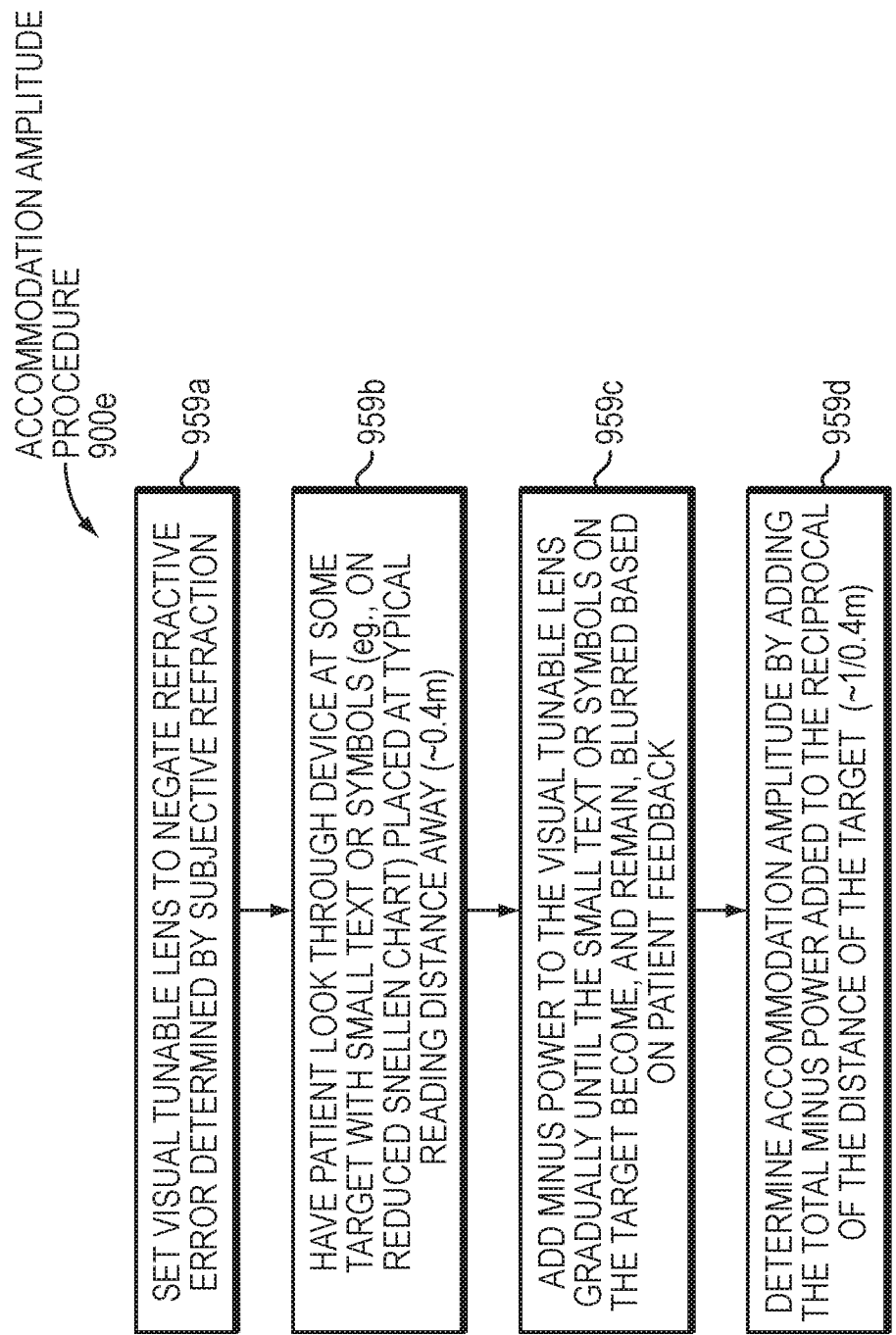
FIG. 9E is a flow diagram illustrating how embodiment devices and methods can be used to measure accommodation amplitude for evaluation of presbyopia.

FIG. 9E is a flow diagram illustrating an example accommodation procedure 900e that shows how embodiment devices and methods can be used to measure accommodation amplitude for evaluation of presbyopia. At 959a, a visual tunable lens is set to negate refractive error of a patient's eye as determined by subjective refraction. At 959b, the patient is requested to view through the apparatus toward a target with small text or symbols, such as a reduced Snellen chart, for example, placed at typical reading distance away from the eye, about 0.4 meters.

At 959c, minus optical power is added to the visual tunable lens gradually until the small text or symbols on the target become, and remain, blurred based on feedback from the patient. At 959d, accommodation amplitude of the patient's eye is determined by adding the total minus power of the visual tunable lens to the reciprocal of the distance of the target (about 1/0.4 m).

While patient feedback in combination with tunable lens adjustments alone may be used to determine accommodation range, a particular advantage of embodiments described herein, including those with both a wavefront sensor and tunable lens in the same apparatus, is that accommodation may be measured in a more automated fashion by taking advantage of wavefront measurements in combination with tunable lens adjustments. As an example, objective and subjective refractive measurements may be performed first, as outlined in FIGS. 8A-8B or in FIGS. 9C-9D. This can provide final corrective prescription for the patient, initially without regard to accommodation range, and the visual tunable lens may be set to the final settings. Subsequently, the apparatus may measure an initial corrected wavefront with these tunable lens settings, and the apparatus may then change the tunable lens focal power very slowly in small steps, allowing for the patient's given eye under test to accommodate while still viewing the fixed target indicia.

At each lens adjustment step, after appropriate accommodation, an additional wavefront measurement can be automatically acquired by the apparatus, saved, and monitored by the determination module. After a sufficient number of steps in focal power, when the determination module eventually determines that the measured wavefront has deviated at least a minimum threshold from the initial corrected wavefront value (or otherwise determines from the wavefront measurements that the eye under test is no longer sufficiently accommodating), then the determination module may determine that a difference between the tunable lens focal power at the final optimized settings and the focal power at the point of maximum accommodation is the accommodation range of the patient's eye. As will be understood in view of this description, accommodation measurements such as those described above may also be performed according to binocular embodiments on both eyes at the same time.

Figure 9F:
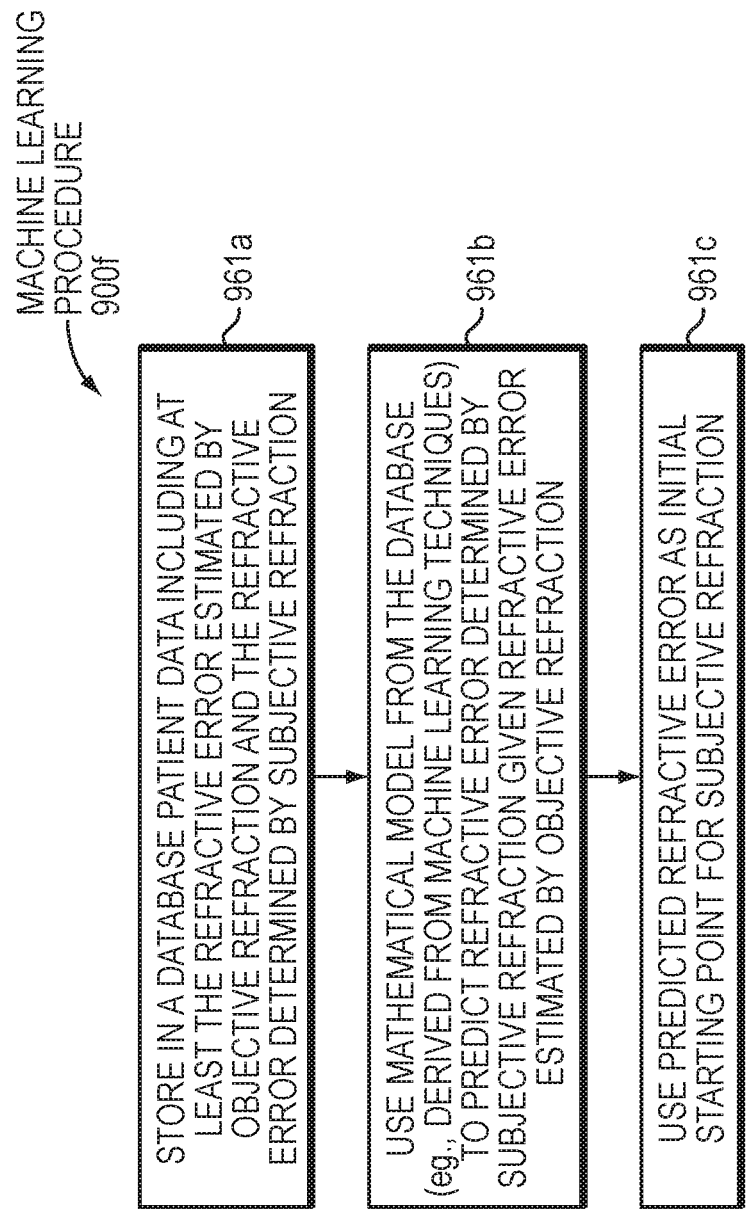
FIG. 9F is a flow diagram illustrating how machine learning can be implemented in embodiment devices and methods to predict subjective refractive preferences of an eye patient based on objective measurements.

FIG. 9F is a flow diagram illustrating an example machine learning procedure 900f showing how machine learning can be implemented in embodiment devices and methods to predict subjective refractive preferences of an eye patient based on objective measurements. At 961a, patient data including at least a refractive error estimated by objective refraction and a refractive error determined by subjective refraction are stored in a database. The database can include the memory 470 in FIG. 4 or a database external to an embodiment apparatus, such as a network database accessed via the network interface 468 in FIG. 4, for example.

At 961b, a mathematical model from the database (e.g., derived from machine learning techniques) is used to predict refractive error determined by subjective refraction given refractive error estimated by objective refraction, as determined according to FIG. 9C, for example. At 961c, predicted refractive error is used as an initial starting point for subjective refraction, as carried out according to FIG. 9D, for example.

FIGS. 10A-10B are flow diagrams illustrating successive parts of a single embodiment procedure 1000 for determining subjective refractive preferences of a patient using embodiment apparatuses. It should be understood that the procedure illustrated in FIG. 9D for subjective refraction is a general procedure that can further include many different variations using embodiment apparatuses. In general, the procedure 1000 in FIGS. 10A-10D is a particular variation that includes iterative determination of coarse and fine subjective refractive preferences for a given eye and allows a patient to interact directly with an apparatus having interactive features to determine the subjective preferences. This can be done with smart, iterative control of visual-tunable-lens vision correction values using interactive patient feedback.

In some embodiments consistent with this disclosure, an optometrist or assistant asks the patient which correction settings for the visual tunable lens are subjectively better, iteratively, as refractive values of the visual tunable lens are changed, similar to the iterative procedure used in standard, optometrist-assisted phoroptry measurements. However, in the procedure 1000, the embodiment apparatus requests that the patient turn the dial 356, which is set to control certain refractive values of the visual tunable lens, iteratively, over coarse and then fine ranges, and the device records the final settings made by the patient to refine subjective preferences. Each time the patient is asked by the device, through the speaker 362 illustrated in FIG. 3, to optimize a setting, the patient turns the dial 356 on the housing of the apparatus, while viewing a target such as a Snellen chart through the apparatus, until the patient is satisfied that he or she has adjusted the dial such that the visual tunable lens is set to the best value for visual acuity. Then, the apparatus automatically records the optimum tunable lens parameter found by the patient, as particularly described hereinafter. In other embodiments, the communication interface 360 in FIG. 3 may be used only to query the eye patient verbally and receive a voice-recognized verbal response from the patient, such as "one" or "two," regarding which subjective, refractive preference is better.

Another feature of the example procedure 1000 is that it illustrates how the orthogonal basis set, spherical equivalent power M, vertical Jackson cross cylinder J0, and oblique Jackson cross cylinder J45 can be set mutually independently by the apparatus. This is in contrast to other embodiments that use the standard clinical S, C, & A basis set referenced hereinabove in relation to FIG. 3, for example. It will be understood that an embodiment apparatus that has control over S, C, and A mutually independently may also control M, J0, and J45 mutually independently by a mathematical transformation.

In general, the procedure 1000 includes setting the visual tunable lens to the optimum settings determined from the objective refraction process using the wavefront aberrometer. An example procedure for determining objective refraction is described in connection with FIG. 9C. Thereafter in the procedure 1000, coarse subjective settings are determined. This is followed by setting the visual tunable lens to the optimum coarse subjective refractive value settings and then determining fine subjective refractive settings. The finer subjective refractive settings are used as the final subjective refractive preference values for the patient, and a refractive prescription may then be determined based on the fine subjective settings, for example. It should be understood that "setting the visual tunable lens," as used herein, can include setting one or more of a plurality of individual tunable lenses optically arranged in series, as described hereinabove in relation to FIG. 1.

In greater detail, in FIG. 10A at 1063, the visual tunable lens is set to optimum objective values for M, J0, and J45 (Mopt, J0opt, and J45opt, respectively) previously determined from objective refraction process based on wavefront aberrometry (see, e.g., FIG. 9C). These optimum objective values can be stored in the memory 470 illustrated in FIG. 4, and the lens settings can be made in response to commands from the processor 472 in FIG. 4, for example. Accordingly, at 1063a-c, M is set to Mopt, J0 is set to J0opt, and J45 is set to J45opt, respectively.

At 1065, coarse subjective settings Mopt', J0opf, and J45opt' are determined. In the procedure 1000, coarse subjective settings are determined in the following manner. At 1065a, the dial 356 is set to control the visual tunable lens such that, over a full range of motion of the dial available to the patient, M will vary over a range of Mopt+/−0.5 dpt while J0 and J45 are maintained constant at J0opt and J45opt, respectively. At 1065b, the apparatus, via the speaker 362, instructs the patient to turn the dial 356 iteratively to optimize subjective visual acuity preference. During this adjustment, a full range of motion of the dial 356 only allows adjustment over the Mopt+/−0.5 dpt range, such that the patient cannot deviate too far from the optimum objectively determined setting. It should be understood that the range of +/−0.5 dpt for the coarse adjustment is an illustrative value, and this value may be changed and set in the apparatus based on further engineering, doctor or optometrist knowledge, machine learning as illustrated in FIG. 9F, demographic factors, or other factors, as necessary. At 1065c, the apparatus then saves this value as the coarse subjective preference Mopt' and sets the visual tunable lens to this value.

At 1065d, the apparatus configures itself to control vertical Jackson cross cylinder J0 in response to a patient adjusting the dial 356. In particular, the apparatus sets itself to adjust J0 over a range of J0opt+/−0.5 dpt as the dial 356 is adjusted over its full range. Meanwhile, the apparatus maintains the visual tunable lens at constant Mopt' and J45opt. At 1065e, the patient is requested, through the speaker 362, to turn the dial 356 iteratively to optimize J0 to an optimum coarse subjective preference value J0opt'. At 1065f, the apparatus then saves J0opt' and sets the visual tunable lens to this value.

At 1065g, a similar procedure is carried out for the parameter J45. The apparatus sets itself to control J45 over a range of J45opt+/−0.5 dpt as the patient turns the dial 356 over its full range, while maintaining constant values Mopt' and J0opt'. At 1065h, the apparatus asks the patient to turn the dial 356 iteratively to optimize visual acuity, and the patient finally settles on a preferred setting. At 1065i, the apparatus saves the setting as the optimum coarse subjective preference value of J45, namely J45opf. With the coarse subjective refractive settings having been determined according to the patient's preferences, at 1067, the apparatus proceeds to determine the fine subjective settings, as illustrated in FIG. 10B, where the procedure 1000 is continued.

In FIG. 10B, in greater detail, at 1069, the apparatus sets the visual tunable lens to the coarse subjective settings determined at 1065 in FIG. 10A, if this has not already been done. Particularly at 1069a-c, the visual tunable lens set to Mopt', J0opf, and J45opt', respectively. At 1071, fine subjective settings are then determined in a manner similar to the manner used to determine the coarse subjective settings, except that the coarse subjective settings are used as the starting point instead of the objective settings. An illustrative, example fine range variation of +/−0.2 dpt variation is used for each parameter. However, as noted above in relation to the coarse variation range, this fine variation range may be selected or set based on additional information or preferences.

At 1071*a*, the apparatus is set to respond to the patient's turning of dial 356 over its full range by controlling M correspondingly over a range of Mopt'±0.2 dpt while maintaining constant J0opt' and J45opf. At 1071*b*, the patient is requested through the speaker to turn the dial iteratively to optimize visual acuity for the particular eye, OD or OS, that is under test. At 1071*c*, the fine subjective preference Mopt" is saved in memory, and the visual tunable lens is set to this value.

At 1071*d*, the apparatus sets itself to control J0 over a range of J0opt'+/−0.2 dpt in response to the dial being changed over its full range, while still maintaining constant Mopt" and J45opf. At 1071*e*, the apparatus asks the patient to turn the dial iteratively to optimize visual acuity. At 1071*f*, the apparatus records the value J0opt" and sets the visual tunable lens to this value. At 1071*g*, the apparatus configures itself to control J45 over a range of J45opt'+/−0.2 dpt in response to the dial being turned over its full range. At 1071*h*, the patient is requested to turn the dial iteratively to optimize visual acuity. At 1071*i*, the apparatus records the optimum fine subjective preference value J45opt" and sets the visual tunable lens to this value.

At 1073, Mopt", J0opt", and J45opt" are then used as the best subjective refractive settings. These values may be set on the apparatus for a final confirmation from the patient that the settings are valid and acceptable. While not illustrated in FIGS. 10A-10B, the apparatus may optionally perform other functions at this point. For example, the apparatus may show the patient corrected and uncorrected views by changing the visual tunable lens, while speaking to the patient accordingly, similar to procedures followed by clinicians during traditional phoroptry. Furthermore, the apparatus may optionally give the patient a further opportunity to indicate that additional adjustments are preferred, either by pressing the trigger switch 397 illustrated in FIG. 3 or by the patient answering "yes" through the microphone 364 illustrated in FIG. 3, for example.

The procedure 1000 may also be repeated for each eye OD and OS in turn. Still further, the procedure 1000 may be modified such that coarse subjective testing is performed on each eye OD and OS in turn, followed by fine subjective testing on each eye in turn. Furthermore, it will be recognized by those skilled in the art of optometry that there are advantages in determining subjective refractive corrections of both eyes at the same time. As is known in the art, a patient's preferred correction for a given eye may differ depending on whether the other eye is looking through a correction lens, is uncorrected, or is blocked at the same time the given eye is evaluated. Accordingly, it will be recognized that, in the binocular arrangements described herein that allow for simultaneous simulated tunable lens correction for both eyes, the procedure 1000 may be modified such that subjective settings are tested for both eyes synchronously. For example, objective wavefront-based optimized tunable lens correction settings may be made for both eyes, followed by the patient or a clinician being directed to change a dial setting that simultaneously adjusts power or another parameter for both eyes together. In this way, a fine or coarse subjective setting may be determined.

Moreover, the procedure may be modified to include appropriate clinician involvement in any case where it is undesirable or impossible for a patient alone to make adjustments to optimize settings. The values Mopt", J0opt", and J45opt" may be reported at an interface similar to the reporting interface screen 354 illustrated in FIG. 3 and used to provide a refractive prescription. Furthermore, information determined from the procedure 1000, such as final, fine subjective refractive preferences, may be provided to a patient, clinician, manufacturer via any of the means described hereinabove or other known means.

It should be understood that the procedure 1000, in other embodiments, can be extended to successively finer adjustments and determinations of subjective refractive preference. Furthermore, higher-order refractive corrections may be determined in a manner similar to that illustrated in the procedure 1000, where a particular visual tunable lens used in the apparatus permits such adjustments. Those with skill in various types of multi-dimensional, iterative optimization, as well as those skilled in the art of optometry, will understand that "coarse" and "fine" subjective settings can further be determined even where the range of optimization (e.g., 0.5 dpt or 0.2 dpt) is the same for both coarse and fine determinations. This is because there is typically value in changing all the parameters to optimize values, followed by re-optimization of the same values, whether with the same or a smaller adjustment range available to the patient.

Moreover, wavefront aberrometry measurements may be interspersed with subjective measurements in any location within the procedure 1000 for a variety of purposes. As described hereinabove, embodiments can perform adjustments of the variable focal power of the visual tunable lens or lenses iteratively in response to successive wavefront measurements to minimize wavefront errors of the light received from the eye or eyes. Wavefront measurements can be performed in a closed-loop fashion, or simply performed two or more times in between subjective measurements taking advantage of the tunable lens. One example includes obtaining an initial wavefront error measurement, setting a tunable lens to correct for the initial wavefront error, and then obtaining one or more secondary or subsequent wavefront measurements.

Performing wavefront measurements on eyes corrected by tunable lenses can allow higher-order corrections to be determined by wavefront aberrometry with greater accuracy that can be done with the same wavefront aberrometry instrument acting alone. As is known, it is useful to know higher-order corrections to apply to an eye for improved vision especially for low-light conditions and other specific cases. As such, embodiments can enable wavefront measurement accuracy commensurate with a very expensive and precise wavefront aberrometer using a relatively much more inexpensive wavefront aberrometer. Use of a tunable lens in combination with a wavefront aberrometer in embodiments can enable more accurate measurement of higher-order aberrations, even with a relatively low-cost embodiment system, because the tunable lens can correct the primary low-order aberrations, thereby cancelling out the contributions of the low-order aberration (typically much larger), thus enabling better detection of the higher-order aberrations with better sensitivity and specificity.

Moreover, embodiments combining tunable lenses with wavefront aberrometry can enable the subjective test (phoroptry) immediately after the objective wavefront aberrometry measurement in situ with the same handheld apparatus applied to the patient. This can provide better patient throughput and accuracy. Further, using embodiments, objective measurements can be performed during the subjective phoroptry measurements. In this case, the objective measurements may be used in a situation in subjective phorptry wherein the patient indicates that it is not clear which tunable lens setting of two or more choices given is better, for example.

Marks, Randall et al., "Adjustable adaptive compact fluidic phoropter with no mechanical translation of lenses," Optics Letters Vol. 35, No. 5, 739-741, Mar. 1, 2010, is hereby incorporated herein by reference in its entirety.

The international Patent Cooperation Treaty (PCT) Applications published as WO 2015/003062 A1 and WO 2015/003086 A1 are hereby incorporated herein by reference in their entireties.

Further, the teachings of all other patents, published applications and references cited herein are incorporated by reference in their entirety.

It should be understood that aspects of embodiments of the invention that are implemented in software may be stored on various types of non-transitory computer-readable media known in the art. The software may be any software that can be loaded and executed by a processor and cause various systems or devices, as applicable, to perform operations as disclosed herein or as equivalent thereto.

While this invention has been particularly shown and described with references to example embodiments thereof, it will be understood by those skilled in the art that various changes in form and details may be made therein without departing from the scope of the invention encompassed by the appended claims.

What is claimed is:

1. An apparatus for determining a property of an eye, the apparatus comprising:
    a housing including a proximal port, the proximal port configured to receive an eye and to receive light from the eye,
    the housing further including a distal port, the proximal and distal ports together forming a visual channel from the proximal port through the distal port, the visual channel providing an open view to enable the eye to see target indicia external to and spaced away from the housing;
    one or more visual tunable optical elements configured to be mounted to the housing, to apply a variable focal power to the light from the eye, and to pass the light along an optical path;
    a wavefront sensor within the housing, the wavefront sensor being configured to receive the light from the eye via the optical path and to measure, based on the eye viewing the target indicia external to and spaced away from the housing via the visual channel providing the open view, a wavefront of the light from the eye;
    a control circuit configured to adjust the variable focal power of the one or more visual tunable optical elements iteratively in response to successive wavefront measurements, in closed-loop manner, to minimize a wavefront error of the light from the eye to determine an objective refractive correction for the eye,
    wherein the control circuit is further configured to adjust, based on the eye viewing the target indicia external to and spaced away from the housing via the visual channel providing the open view, the variable focal power of the one or more visual tunable optical elements to a subjective refractive preference of a person having the eye, the subjective refractive preference differing from the objective refractive correction; and
    a determination module configured to determine a property of the eye based on the objective refractive correction and the subjective refractive preference.

2. The apparatus of claim 1, wherein the housing is configured to be gripped by at least one hand of a person having the eye to support a full weight of the apparatus during use.

3. The apparatus of claim 1, wherein the determination module is further configured to determine a refractive correction to be applied to the eye.

4. The apparatus of claim 1, wherein the determination module is further configured to determine an accommodation range of the eye as a function of a plurality of wavefront measurements of the light from the eye.

5. The apparatus of claim 1, further comprising a manual control configured to be adjustable by the person having the eye to adjust the variable focal power of the one or more visual tunable optical elements in accordance with the subjective refractive preference of the person having the eye.

6. The apparatus of claim 1, further comprising a communication interface configured to query the person having the eye, or receive a response from the person, regarding the subjective refractive preference.

7. The apparatus of claim 1, wherein the one or more visual tunable optical elements are further configured to apply a variable spherical power, astigmatic power, and axis mutually independently.

8. The apparatus of claim 1, wherein the one or more visual tunable optical elements are further configured to apply a spherical equivalent power, vertical Jackson cross cylinder, and oblique Jackson cross cylinder mutually independently.

9. The apparatus of claim 1, wherein the one or more visual tunable optical elements include at least one of a liquid-filled lens, an electro-wetting lens, an Alvarez lens pair, spatial light modulator, deformable mirror, lens with power that varies spatially, multi-lens system that changes lens distances or orientations relative to each other to tune optical power, or a tunable Fresnel lens.

10. The apparatus of claim 1, wherein the one or more visual tunable optical elements include a two-element optic configured to apply the variable focal power as a function of lateral displacement of the two elements with respect to each other.

11. The apparatus of claim 1, wherein the determination module is further configured to predict the subjective refractive preference of the person having the eye based on the objective refractive correction.

12. The apparatus of claim 11, wherein the determination module is further configured to predict the subjective refractive preference based on a demographic or physical attribute of a person having the eye, the demographic or physical attribute comprising at least one of an age, gender, ethnicity, weight, height, occupation, or another demographic trait of the person having the eye; or a retinal image quality, axial length, iris color, topography, corneal curvature, or aberration of higher order than spherical or cylindrical aberration of the eye.

13. The apparatus of claim 12, wherein the determination module is further configured to predict the subjective refractive preference using a correlation developed from a database including respective demographic or physical attributes and respective objective eye properties of a plurality of eye patients.

14. A method for determining a property of an eye, the method comprising:
    applying a variable focal power to light received from an eye, via a proximal port of a housing configured to receive the eye, using one or more visual tunable optical elements;

passing to the eye, via an open view visual channel from a distal port of the housing to the proximal port, through the one or more visual tunable optical elements, light from target indicia external to and spaced away from the housing;

passing the light received from the eye along an optical path;

measuring, based on the eye viewing the target indicia external to and spaced away from the housing via the visual channel providing the open view, a wavefront of the light from the eye, the light received via an optical path from the proximal port;

adjusting, using the one or more visual tunable optical elements, the variable focal power iteratively in response to successive wavefront measurements, in closed-loop manner, to minimize a wavefront error of the light from the eye to determine an objective refractive correction for the eye;

adjusting, based on the eye viewing the target indicia external to and spaced away from the housing via the visual channel providing the open view, the variable focal power of the one or more visual tunable optical elements to a subjective refractive preference of the person having the eye, the subjective refractive preference differing from the objective refractive correction; and determining a property of the eye based on the objective refractive correction and the subjective refractive preference.

15. The method of claim 14, further including enabling a person having the eye to grip the housing to support a full weight of the housing and one or more visual tunable optical elements during receiving light from the eye.

16. The method of claim 14, wherein the proximal port is a first proximal port, the eye is a first eye, and the one or more visual tunable optical elements include a first visual tunable lens, the method further including:

receiving a second eye at a second proximal port of the housing;

receiving light from the second eye through the second proximal port, wherein the first and second proximal ports are first and second ports of a binocular housing; and applying a variable focal power to the light from the second eye using a second visual tunable lens.

17. The method of claim 14, wherein determining the property of the eye includes calculating a refractive correction to be applied to the eye.

18. The method of claim 14 wherein determining the property of the eye further includes calculating an accommodation range of the eye as a function of a plurality of wavefront measurements of the light from the eye.

19. The method of claim 14, wherein adjusting the variable focal power of the one or more visual tunable optical elements to the subjective refractive preference is in response to manual control by the person having the eye.

20. The method of claim 14, further including predicting the subjective refractive preference of the person having the eye based on the objective refractive correction.

21. The method of claim 20, wherein predicting the subjective refractive preference further includes predicting based on a demographic or physical attribute of the person having the eye, the demographic or physical attribute comprising at least one of an age, gender, ethnicity, weight, height, occupation, or another demographic trait of the person having the eye; or a retinal image quality, axial length, iris color, topography, corneal curvature, or aberration of higher order than spherical or cylindrical aberration of the eye.

22. The method of claim 21, wherein predicting the subjective refractive preference includes using a correlation developed from a database including respective demographic or physical attributes and respective objective eye properties of a plurality of eye patients.

23. The method of claim 14, wherein measuring the wavefront of the light from the eye includes measuring the wavefront before or during the further adjusting the variable focal power of the one or more visual tunable optical elements to the subjective refractive preference.

24. The apparatus of claim 1, wherein the wavefront sensor is further configured to measure the wavefront of the light from the eye before or during an adjustment of the variable focal power of the one or more visual tunable optical elements to the subjective refractive preference.

25. The apparatus of claim 1, wherein the one or more visual tunable optical elements include two or more tunable lenses configured to apply, to the light from the eye, spherical power and astigmatic power with variable axis via respective lenses of the two or more tunable lenses.

26. An apparatus for determining a property of an eye, the apparatus comprising:

a housing including a proximal port, the proximal port configured to receive an eye and to receive light from the eye, the housing further including a distal port, the proximal and distal ports together forming a visual channel from the proximal port through the distal port, the visual channel providing an open view to enable the eye to see target indicia external to and spaced away from the housing;

one or more visual tunable optical elements configured to be mounted to the housing, to apply a variable focal power to the light from the eye, and to pass the light along an optical path;

a wavefront sensor within the housing, the wavefront sensor being configured to receive the light from the eye via the optical path and to measure a wavefront of the light from the eye;

a control circuit configured to adjust the variable focal power of the one or more visual tunable optical elements iteratively in response to successive wavefront measurements, in closed-loop manner, to minimize a wavefront error of the light from the eye to determine an objective refractive correction for the eye, wherein the control circuit is further configured to adjust the variable focal power of the one or more visual tunable optical elements to a subjective refractive preference of a person having the eye, the subjective refractive preference differing from the objective refractive correction; and a determination module configured to determine a property of the eye based on the objective refractive correction and the subjective refractive preference, wherein the determination module is further configured to predict the subjective refractive preference of the person having the eye based on the objective refractive correction.

27. A method for determining a property of an eye, the method comprising:

applying a variable focal power to light received from an eye, via a proximal port of a housing configured to receive the eye, using one or more visual tunable optical elements;

passing to the eye, via an open view visual channel from a distal port of the housing to the proximal port, through the one or more visual tunable optical elements, light from target indicia external to and spaced away from the housing;

passing the light received from the eye along an optical path;

measuring, with the visual channel providing the open view, a wavefront of the light from the eye, the light received via an optical path from the proximal port;

adjusting, using the one or more visual tunable optical elements, the variable focal power iteratively in response to successive wavefront measurements, in closed-loop manner, to minimize a wavefront error of the light from the eye to determine an objective refractive correction for the eye;

adjusting, with the visual channel providing the open view, the variable focal power of the one or more visual tunable optical elements to a subjective refractive preference of the person having the eye, the subjective refractive preference differing from the objective refractive correction;

determining a property of the eye based on the objective refractive correction and the subjective refractive preference; and predicting the subjective refractive preference of the person having the eye based on the objective refractive correction.

* * * * *